United States Patent
Behling

(10) Patent No.: US 9,538,979 B2
(45) Date of Patent: Jan. 10, 2017

(54) X-RAY DETECTION

(71) Applicant: KONINKLIJKE PHILIPS N.V., Eindhoven (NL)

(72) Inventor: Rolf Karl Otto Behling, Hamburg (DE)

(73) Assignee: KONINKLIJKE PHIIPS N.V., Eindhoven (NL)

( * ) Notice: Subject to any disclaimer, the term of this patent is extended or adjusted under 35 U.S.C. 154(b) by 0 days.

(21) Appl. No.: 14/911,745

(22) PCT Filed: Aug. 27, 2014

(86) PCT No.: PCT/EP2014/068141
§ 371 (c)(1),
(2) Date: Feb. 12, 2016

(87) PCT Pub. No.: WO2015/032664
PCT Pub. Date: Mar. 12, 2015

(65) Prior Publication Data
US 2016/0183907 A1    Jun. 30, 2016

(30) Foreign Application Priority Data

Sep. 5, 2013 (EP) .................................. 13183089

(51) Int. Cl.
| | |
|---|---|
| H01J 35/00 | (2006.01) |
| A61B 6/00 | (2006.01) |
| H05G 1/46 | (2006.01) |
| H01J 35/10 | (2006.01) |
| H01J 35/18 | (2006.01) |
| A61B 6/04 | (2006.01) |

(52) U.S. Cl.
CPC ............. *A61B 6/585* (2013.01); *A61B 6/4035* (2013.01); *A61B 6/4266* (2013.01); *A61B 6/586* (2013.01); *H01J 35/00* (2013.01); *H01J 35/10* (2013.01); *H01J 35/18* (2013.01); *H05G 1/46* (2013.01); *A61B 6/0407* (2013.01); *A61B 6/4441* (2013.01); *A61B 6/4464* (2013.01); *A61B 6/54* (2013.01)

(58) Field of Classification Search
CPC .......... A61B 6/4035; A61B 6/54; H01J 35/00; H05G 1/46
See application file for complete search history.

(56) References Cited

U.S. PATENT DOCUMENTS

| | | | |
|---|---|---|---|
| 4,172,223 | A | 10/1979 | Ishijima |
| 4,918,714 | A | 4/1990 | Adamski |
| 5,293,415 | A | 3/1994 | Hartley |
| 2004/0109536 | A1 | 6/2004 | Shefer |
| 2004/0247080 | A1 | 12/2004 | Feda |
| 2009/0067578 | A1 | 3/2009 | Behling |

FOREIGN PATENT DOCUMENTS

WO    2012069944 A1    5/2012

*Primary Examiner* — David J Makiya
*Assistant Examiner* — Dani Fox

(57) ABSTRACT

Rotating anode X-ray tubes degrade over time because of the action of the electron beam altering the surface of the focal spot area of a rotating anode. This causes a degradation in a resulting object image, when the source is used in an imaging application. An X-ray tube housing assembly is discussed which allows the correction of such effects. In particular, an additional beam of the X-radiation, which is not used for imaging, may be used to correct such effects.

18 Claims, 10 Drawing Sheets

X-RAY DETECTION

CROSS-REFERENCE TO PRIOR APPLICATIONS

This application is the U.S. National Phase application under 35 U.S.C. §371 of International Application No. PCT/EP2014/068141, filed on Aug. 27, 2014, which claims the benefit of European Patent Application No. 13183089.5, filed on Sep. 5, 2013. These applications are hereby incorporated by reference herein.

FIELD OF THE INVENTION

The present invention relates to X-ray detection.

BACKGROUND OF THE INVENTION

In rotating anode tube X-ray sources electrons are accelerated between a cathode and the rotating anode across a kilo-Volt potential difference so that they impact onto the focal track of the rotating anode. In the process, X-rays are generated, which are said to emanate from a "focal spot" at the point of electron beam impact on the rotating anode. Due to the energy dissipated in the impact, the rotating anode's surface may be modified in the process, and small pits and cracks may begin to appear.

As a consequence, the X-ray yield and spectrum of the tube may change over the course of its lifetime, which may have an impact on the application in which the tube is used. The trend in modern X-ray tube applications is for the instantaneous power applied to the rotating anode to increase, commensurately with the increase of the gantry speed (in a CT system).

Furthermore, the shrinking of the detector cells and the focal spot (to allow better spatial resolution), and the widening of the anode angle (for widened detector coverage) lead to an increased power density at the focal spot of rotating anode X-ray tube. The rate of alteration of the rotating anode's surface caused by the electron beam is only likely to increase in the future.

In US 2009/0067578 A1, a rotating anode is described with a structure comprising slits, which can be detected if a structure placed on the anode passes the focal spot. Thus, properties of the focal spot can be determined from changes of the detected signal during operation of the X-ray tube.

SUMMARY OF THE INVENTION

A spectral detection CT system can suffer from the unknown spectral variability of a rotating anode X-ray source caused by changes in the target material of the rotating anode. In a rotating anode X-ray source, the spectral variability may occur with a characteristic time variability of between 10 and 100 ms, as a roughened target moves under the electron beam through the focal spot. The target is roughened through the repeated action of an electron beam impacting the rotating anode and dislodging some of the anode's surface over many exposure cycles. This may create high frequency alterations of the X-ray spectrum, which could degrade the image quality of an imaged object.

It has also been shown that, due to thermal expansion of the rotating anode as thermal energy caused by decelerating electrons dissipates into the anode, the focal spot's position on the rotating anode may drift away from its desired position. The size and X-ray intensity distribution of the resulting beam may also vary in an undesired way. It would be helpful to allow for correction of the effect of thermal anode heating.

Finally, tube voltage and/or current as a key technique factor are usually measured in an X-ray system using a costly and bulky resistive voltage divider. Enhanced compactness and a reduced measurement cost would be desirable.

Thus, there may be a need for an X-ray source to provide a correction signal containing information that can be used to correct an X-ray image, wherein the correction signal itself has not been influenced by an imaged object.

The objects of the present invention are solved by the subject-matter of the independent claims, wherein further embodiments are incorporated in the dependent claims. It should be noted that the following described aspects of the invention apply also to the X-ray imaging system, and the method.

According to the invention, an X-ray tube housing assembly is provided which is operable to provide a signal, the X-ray tube housing assembly comprising an X-ray tube, generating X-radiation from a focal spot, a reference filter, a reference detector, and a controller. The X-radiation comprises a main portion, and a reference portion, wherein the main portion is distinct from the reference portion. The main portion and the reference portion are between a minimum and a maximum take-off angle, being angles of elevation from a vertex at the focal spot, subtended by a base plane. The minimum take-off angles of the reference portion and main portion are equal to each other, and the maximum take-off angles of the reference portion and main portion are equal to each other. The reference filter is configured to filter the reference portion before detection of the reference portion by the reference detector. Furthermore, the reference detector is configured to detect the reference portion to provide a reference signal, and the controller is configured to calculate a signal, based on the reference signal.

Such an X-ray source allows variations in the X-rays emitted by the X-ray source caused by alterations to the rotating anode to be measured and corrected, because the reference detector detects X-rays from the reference portion of the X-rays, which has the same spectral characteristics and spatial intensity profile as the main portion of the X-rays, which can be used to illuminate an object to be imaged, for example, a patient in a CT scanner.

The reason why X-rays from the reference portion can be used to correct X-radiation in the main portion is that both portions of radiation are taken from the same X-ray tube, pass through the same type of reference filter and detector, and the "take-off" and "fan" angles at which portions are taken from the rotating anode of the X-ray tube are also the same.

A signal provided in this way from the X-ray tube assembly can give information which allows the correction of the effects mentioned previously, namely, but not limited to, spectral variability caused by roughness of the beam target, drift of the focal spot caused by the heating of the rotating anode, and measurement of tube voltage and other important technique factors.

According to an exemplary embodiment of the invention, the X-ray tube housing assembly comprises an X-ray housing with a reference X-ray window and a main X-ray window, so that, in operation, the reference X-ray window provides a reference beam, and the main X-ray window provides a main beam.

In this embodiment, the windows (or apertures) form well-defined beams from the reference and main X-ray portions, for directing at the reference detector and the target, respectively.

According to another exemplary embodiment of the invention, the X-ray tube housing assembly comprises an object opaque to X-rays placed inside the vacuum tube, so as to separate the X-rays into the reference beam and the main beam.

In this embodiment, well-defined reference beams and main beams can be generated without requiring extra hardware within the casing of the X-ray tube housing assembly itself: the means for dividing the beams into reference and main beam are provided inside the X-ray tube.

According to another exemplary embodiment of the invention, the X-ray tube housing assembly further comprises an attenuator placed in-between the reference detector and the reference filter.

The attenuator prevents the saturation of the reference detector element, which are typically pixels in a photon counter. Therefore, the reference detector can detect the X-ray flux accurately. The attenuator may be made from of a material with a low atomic number, such as Teflon® or beryllium, which are have a limited X-ray filtering effect, but a significant X-ray attenuation effect.

According to another exemplary embodiment of the invention, the reference filter can be can be substituted between exposures.

In an exemplary application of a CT scanner, different object imaging regimes use different powers of X-rays, dependent on the size of a patient, for example. This requires the substitution of the filter at the imaged object side. It would be convenient to be able also to substitute the reference filter so that it matches the patient filter at any one time. In this way, the reference beam arriving at the reference detector will have passed through the same type of filter as the main beam.

According to a further exemplary embodiment of the invention, the X-ray tube housing assembly further comprises an anti-scatter grid that is located in-between the reference detector and the attenuator, and that is focused onto the focal spot.

The provision of an anti-scatter grid prevents off-centre X-rays from reaching the reference detector. This improves the quality of the reference signal. Such off-centre radiation could also degrade the quality of a reference beam, as a true representation of the radiation emitted before passing through the object to be imaged, and could therefore degrade the quality of the correction signal derived from the reference signal.

According to a further exemplary embodiment of the invention, an X-ray blocker is provided, which comprises a spatial resolving slit, and is thus configured together with the reference detector to form a one-dimensional focal spot slit camera to detect a position of the focal spot from an edge of a spatial intensity distribution.

According to an embodiment of the invention, an X ray tube assembly is provided with opaque wires placed in front of the reference detector to form a spatial resolving stripe, which is thus configured, together with the reference detector, to detect a position of the focal spot from a pattern of an intensity distribution.

According to another exemplary embodiment of the invention, two spatial resolving slits are positioned orthogonally, to form a two-dimensional focal spot slit camera, which is configured to detect, in operation, the position of the focal spot from of a pattern of the measured reference beam.

The presence of two orthogonal slit cameras positioned across the fan beam allows focal spot drift along the base plane, and above and below the base plane to be detected. This allows the drift of the focal spot to be identified in two dimensions. The base plane in this sense refers to the plane of rotation of the rotating anode.

According to a further embodiment, the reference filter of the X-ray tube housing assembly has a plurality of filters with different filter values, and the one- or two-dimensional focal spot slit cameras comprise a further plurality of attenuators with different attenuator values so that the reference detector of the slit camera detects the reference beam behind a plurality of combinations of attenuators and filters.

In this embodiment, the reference detector receives the reference beam which has been filtered through combinations of different filter values and different attenuators. Because the photon flux may vary according to the application protocol of the X-ray system, for example, different image filters may be used dependent on the size of an object to be imaged, such as a patient, and to make sure that there is always a well-illuminated line array of reference detector pixels along the combinations of filters and attenuators across the fan beam, which are neither over nor under-radiated. Each "sector" is defined by a filter and attenuator combination.

According to a further exemplary embodiment of the invention, the filter and attenuator combinations cover the entire reference beam ($\beta$).

In this embodiment, for each possible filter in the used beam, there will be a corresponding filter in the reference beam. The spectrum can therefore be measured across the width of the beam, even when X-ray intensities of widely differing values are applied.

According to a further exemplary embodiment, an X-ray tube housing assembly according is provided with a plurality of one-dimensional or two-dimensional focal spot slit cameras. Together, these form a multi-slit focal spot camera. At least a first and a second slit of the slits of the plurality of one- or two-dimensional focal-spot slit cameras are offset relative to a pixel boundary of the reference detector.

Therefore, according to this embodiment, upon movement or a change of shape of the focal spot, these multiple slit cameras generate different signal ratios. An optimal signal ratio may be used for detection of the distortion. This allows pixels of a larger size to be used in the detector.

According to a further exemplary embodiment of the invention, the controller is configured to calculate from at least one output of at least one reference detector, at least one parameter from the group consisting of: spectral variability, tube voltage, the position of the focal spot, the size of the focal spot, the intensity of the focal spot, the tube current, the tube ageing, the dynamic anode rotational instability, the periodic anode rotational instability, magnetic distortions of the position or shape of the focal spot, and gravitational distortions of the shape or position of the focal spot.

Therefore, signals characterizing the reference beam can be calculated. These signals may fall into at least three categories:

Firstly, imperfections occurring at a high frequency associated with rotating anode damage caused by the electron beam may be measured across the reference beam and recorded. This allows the high frequency imperfections caused by rotating anode imperfections to be corrected in the object image, either in real-time or in image post-processing.

Secondly, changes occurring at a lower rate, principally due to rotating anode heating may be tracked. Such lower rate effects may principally manifest themselves in the form of a deviation of the location of the focal spot over several seconds, caused by expansion or contraction of the rotating anode due to heating or cooling. Signals relating to thermal expansion may be "fed-back" in a control loop to electrodes inside the X-ray tube, for compensating for the thermal drift.

Alternatively, such thermal drift signals may provide an extra correction signal for the object image.

Finally, parameters related to the tube voltage or the tube current, which are important for the operation of the X-ray examination apparatus, may be captured. These parameters may therefore be captured without extensive extra-circuitry as is usually required.

In addition, when taking a current measurement using the reference beam, only the current in the reference beam is measured (the current in the main beam will be correlated to the current in the reference beam), rather than the total current entering the X-ray tube housing assembly.

According to a further exemplary embodiment, the reference filter and reference detector are comprised within a vacuum tube.

Placing the reference detector and the reference filter inside the vacuum tube allows the reference beam arrangement to be made more compact.

According to the invention, a plurality of reference beams is provided. Each of the plurality of reference beams is associated with a reference detector, and the tube housing assembly is configured, in operation, to select or to combine signals from the plurality of reference beams.

Therefore, it is possible to select the strongest reference signal, or to improve the signal-to-noise ratio of a calculated signal by combining information from the beams.

According to the invention, an X-ray imaging system is also provided with: an X-ray tube housing assembly; a changeable pre-object X-ray filter; a post-object detector; and a processing unit. The X-ray tube housing assembly is an X-ray tube housing assembly as previously described. The pre-object X-ray filter matches at least one reference filter value in the X-ray tube housing assembly. The post-object detector is the same type as the reference detector in the X-ray tube housing assembly. Further, the processing unit receives the signals from the X-ray tube housing assembly and uses them to correct data from the post-object detector.

In the X-ray imaging system as described, the reference beam is exposed to the same type of element as the imaging beam (main beam). Therefore, degradations in the beam quality caused by rotating anode degradation can be accurately measured and compensated for.

According to an exemplary embodiment of the invention, an X-ray imaging system is provided. The pre-object X-ray filter is different from the at least one reference filter in the X-ray tube housing assembly.

When the X-ray imaging system uses different filter values on the pre-patient and post-patient side, the system is simplified because there is no need to ensure that the filters are matched for each exposure.

According to the invention, a method is also provided for determining changes in the X-ray emission characteristic of an X-ray tube. The method comprises the steps of:
a) Generating X-radiation from the focal spot of an X-ray tube, wherein the X-radiation comprises a main portion, and a reference portion, wherein the main portion is distinct from the reference portion; wherein the main portion and the reference portion are between a minimum ($\alpha_{min,MAIN}$, $\alpha_{min,REF}$), and a maximum ($\alpha_{max,MAIN}$, $\alpha_{max,REF}$) take-off angle, being angles of elevation from a vertex at the focal spot, subtended by a base plane; wherein the X-radiation comprises a main portion, and a reference portion, wherein the minimum take-off angles of the reference portion and main portion ($\alpha_{min,REF}$, $\alpha_{min,MAIN}$) are equal to each other, and the maximum take-off angles of the reference portion and main portion are equal to each other ($\alpha_{max,REF}$, $\alpha_{max,MAIN}$);
b) Filtering the reference portion using a reference filter.
c) Detecting the reference portion.
d) Outputting a reference signal representing a characteristic of the reference portion.
e) Calculating a correction signal.
f) Outputting the correction signal.

The method, as defined above, allows a correction signal to be provided which can be used to compensate for the effects of rotating anode aging or heating on an X-ray object image. Additionally, the correction signal obtained via this method can be used to derive important operational information such as tube current and tube voltage.

According to the invention, imperfections in an X-ray tube are characterized using a distinct reference portion (beam) from an X-ray tube. The reference beam is distinct from the X-ray portion (beam) used to image an object, for example a patient. Any position of the reference detector around the base plane (defined by the azimuth angle φ of the rotating anode) is possible, provided the position is distinct from the main beam used for object imaging.

The two-dimensional area of the reference detector on the one hand, and the two-dimensional focal spot area on the other hand, define the reference portion. The minimum take-off angle, and the fan angle, of the reference beam should be equal to those of the imaging beam. This is because the spectrum and the intensity distribution of the photons which are emitted from the rotating anode exhibits polar symmetry around the normal to the plane, in which the focal spot is located.

If a filter is used in the reference beam which is the same as in the main beam, this ensures equal beam quality.

In the foregoing discussion, the division of the X-rays from the source into a main portion and a reference portion was discussed. It is to be understood that the term "main portion" simply refers to that sector of the X-rays emitted from the rotating anode that is directed towards an object of interest, and which is then measured by a detector on a measurement side.

Likewise, it is to be understood that the term "reference portion" simply defines another sector of the emitted X-rays which is detected by a reference detector. The reference portion and the main portion of the X-rays are distinct from each other.

Furthermore, it is to be understood that that more than one reference detector may be placed inside the X-ray tube housing assembly. In this case, there will be more than one reference portion, one for each reference detector. If multiple reference portions (and reference beams) are provided, each of them may have a different filter. In this way, a filter matched to the filter used in the main beam may be selected automatically, without user intervention.

It is further to be understood that the term "minimum take-off angle" defines an angle between an edge of either the main portion or the reference portion, and the base plane of the rotating anode. In addition, the "maximum take-off angle" defines an angle between the opposite edge of the reference portion or the main portion, and the base plane of the rotating anode. The minimum and maximum take-off angles of the reference portion are angles of elevation from a vertex located at the focal spot.

It is further to be understood from the foregoing discussion that the reference beam and the main beam are defined according to windows in the envelope of the X-ray tube or in the X-ray tube housing assembly.

It is further to be understood that the base plane is defined as the plane tangential to the frusto-conical (chamfered) surface of the rotating anode, upon which the focal spot is positioned. In other words, the base plane is in the same plane as a chamfer angle of the rotating anode onto which the electron beam is directed. As the area of the focal spot, and the area in which it may move is usually very small in comparison with the area of the frusto-conical section, a good approximation is that that the motion of the focal spot occurs around a centre position (vertex) on a flat plane. The effects of this approximation do not materially affect the operation of the present invention. The approximation does, however, serve to allow an easier visualization of the geometry.

Of course, the X-ray tube assembly may be used inside a CT system. In a CT system, an X-ray tube assembly rotates about the patient and generates a fan beam of X-rays. A detector system which converts the X-rays attenuated by an imaged object to electrical signals rotates opposite to it on a gantry. Then, a computer system reconstructs an image of the patient's anatomy.

Of course, the general technique discussed is not simply applicable to a CT system. Many other types of X-ray system may benefit from the application of a reference beam to correct imperfections occurring in the X-ray tube, for example, a C-arm system.

The technique could also be applied to systems such as the X-ray scanners used in industrial manufacturing systems, or in passenger luggage systems. The application should not be considered as being limited simply to medical imaging systems.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
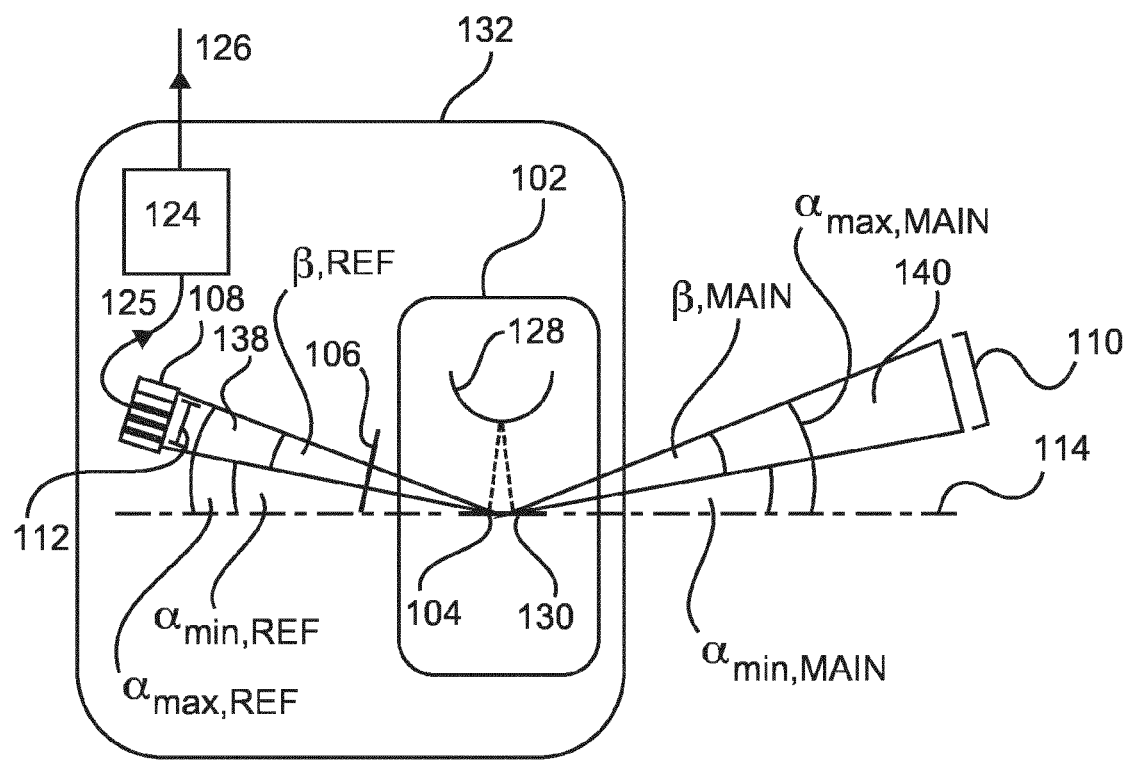
FIG. 1 schematically illustrates an example of an X-ray tube housing assembly.

FIG. 1 schematically illustrates an X-ray tube housing assembly 132 according to the invention. The X-ray tube housing assembly 132 comprises an X-ray tube 102 contained inside the source. The X-ray tube has a sealed envelope maintaining a vacuum inside it. Inside the tube there is a cathode 128 arranged in proximity to a rotating anode 130.

When an appropriate voltage is applied across the cathode and rotating anode, an electron beam travels through the vacuum and impinges on the rotating anode 130. The rotating anode, as used in a CT system, has a frusto-conical (segment of a cone) form, an example of which is shown in FIG. 3c. The point at which the X-ray beam impinges on the rotating anode 130 is known as the focal spot 104. The focal spot is located on the slanted side (chamfer) of the frusto-conical form. X-rays are emitted from the focal spot as a result of the rapid deceleration and acceleration of the electrons, leading to the emission of "Bremsstrahlung" radiation.

Arranged inside the X-ray tube housing assembly 132 is a reference filter 106, and a reference detector 108. The reference detector has an X-ray view of the focal spot 104, through the reference filter 106.

The reference detector 108 outputs a reference signal 125 which is linked to the level of X-ray flux incident on the pixels of the reference detector.

The controller is configured to receive the reference signal and perform calculations, thereby outputting a signal 126, which is based on the reference signal.

It will be noted that, in operation, the cathode 128 emits electrons towards the target area on the rotating anode. The electrons impinge on the target area, thus generating X-ray radiation (X-rays). The X-ray photons are emitted in a random way, causing an intensity distribution extending into the half-space above the focal spot. In FIG. 1, this is illustrated by means of two portions 112 and 110. Portion 112 is also referred to as the "reference portion", and portion 110 is referred to as the "main portion". The main portion 110 is typically emitted from the X-ray tube housing assembly 132 and, in an X-ray system, is arranged to be incident on an object to be imaged.

The reference portion 112 is emitted from the X-ray tube 102 through the reference filter 106 and is received by the reference detector 108. As illustrated, a base plane 114, subtends angles of elevation defining the main and reference portions. The base plane is the plane tangential to the edge of the frusto-conical section of the rotating anode upon which the focal spot is located.

Figure 6:
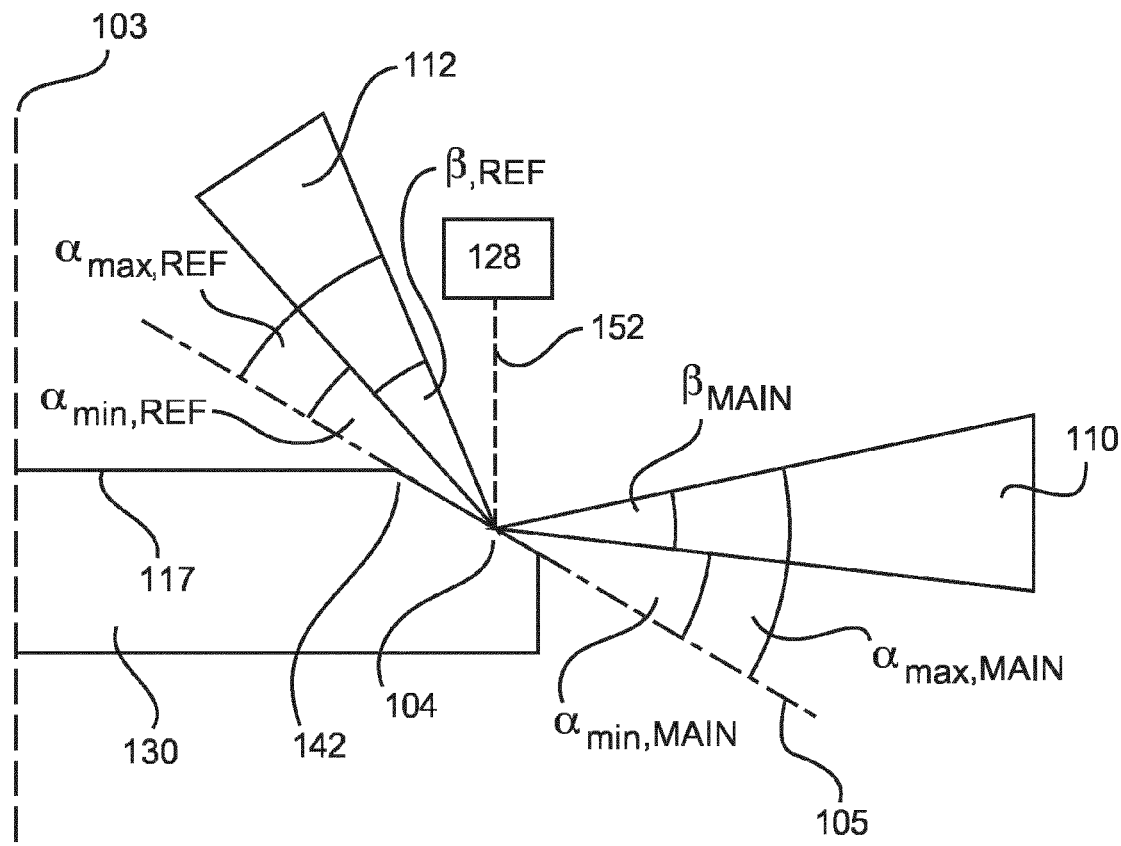
FIG. 6 shows a reference portion and a main portion emitted from a rotating anode.

The surface of the focal spot covers, microscopically, a very small proportion of the chamfered portion, that is to say, it is a fraction of the frusto-conical portion of the rotating anode. The base plane in FIG. 6 is the plane tangential to the focal spot. Stationary anodes are usually flat. In this case, where the invention can also be applied, the base plane is simply the focal spot plane.

It will be appreciated by the reader that for graphical simplicity, the base plane and the resulting angles can be modeled as being horizontal, as shown in FIG. 1. The differences arising from the base plane being modeled as horizontal, on the one hand, and tilted into the tangent of the frusto-conical (chamfered) edge, on the other hand, do not affect the invention.

The reference portion 112 can be thought of as being defined between the two-dimensional area occupied on one side by the front of the reference detector 108 and on the other side the area occupied by the focal spot.

The main portion 110 may be thought of as being defined in the regions between the focal spot on one side, and the front of an imaging detector which is not claimed in this embodiment, and is not shown in FIG. 1. It will be appreciated by the reader that, according to this definition, the reference portion and the imaging portion will be distinct. This is because the reference detector cannot physically occupy the space in front of, or behind, where the imaging detector is placed, because it would obscure the imaging detector.

As illustrated in FIG. 1, the reference portion 112 has a minimum ($\alpha_{min,REF}$) and a maximum ($\alpha_{max,REF}$) take-off angle. The take-off angle of the reference portion is defined as the angle of elevation from the vertex, which vertex is located at the focal spot, subtended by the base plane 114.

It will be appreciated that there is a minimum take-off angle and a reference take-off angle defining the boundary of the reference portion. Subtracting the minimum reference take-off angle from the maximum reference take-off angle yields the fan angle $\beta'$.

As is also illustrated in FIG. 1, the main portion also has a minimum and a maximum take-off angle. Likewise, the maximum and minimum take-off angle of the main portion can be subtracted from each other, yielding the main fan angle $\beta$. It will be appreciated that the reference portion fan angle $\beta'$ is related to the area of the reference detector 108 and the area of the focal spot 104. Likewise, it will also be appreciated that the fan angle $\beta$ of the main portion is defined by the area of the focal spot and the area of the eventual imaging detector.

It is an essential aspect of the invention that the minimum take-off angle ($\alpha_{min,REF}$) of the reference portion and minimum take-off angle ($\alpha_{min,MAIN}$) of the main portion are equal. Likewise, it is an essential aspect of the invention that the fan angle of the reference portion $\beta'$ is equal to the fan angle of the main portion $\beta$. This is because if it assumed that the anode surface can be approximated as flat (for example not curved or otherwise distorted), the spectrum is only dependent on the take-off angle with the anode surface (due to polar symmetry). The reference portion can therefore be taken off at any position outside of the useful beam, provided the previous angular conditions are met.

As the electrons impinge on the rotating anode, X-rays are created. For medical X-rays and tungsten targets, dependent on the tube voltage, the mean depth of interaction of the electrons is between 2 to 10 micrometers. Therefore, the X-rays have to pass through the material of the rotating anode target. The intensity distribution around the rotating anode shows a "heel effect", of which the characteristics are a lack of photon flux close to the anode shadow. This is exemplified in FIG. 5b. The anode's surface roughens due to thermal cycling of the focal spot. The roughness can lie in the range of between 10 to 100 micrometers, and the roughening effect worsens as the tube ages, which, commensurately, causes an increase in the heel effect. The rate at which this effect becomes worse increases as the tube power increases. Therefore, the photon flux and the spectrum of the X-ray beam are dependent on the take-off angle, the tube history, and in rotating anode tubes even the phase of the anode rotation through the azimuth plane, because the local condition of the anode material travelling through the electron beam will vary over time.

It is noted that in an exemplary embodiment, it is that the reference filter 106 is of the same type as in the main portion of the X-rays which eventually passes through the object to be imaged (e.g. a patient). Because the minimum take-off angle and fan angle of the reference portion is equal to the minimum take-off angle and fan angle of the main portion, and because the X-rays from the reference portion will have passed through the same type of filter as the radiation from the main portion, the degradation of the beam quality arriving at the reference detector 108 is equal to the degradation of the beam quality arriving at a detector in the main beam, which is not further illustrated.

In an alternative embodiment, the reference filter 106 is of a different type to the filter used in the main portion.

Therefore, the reference beam provides additional information about the condition of the X-ray tube's rotating anode, which can be used to correct the image information which is imaged using the main portion. This arrangement permits variations in the X-ray beam caused by the X-ray tube 102 to be measured and corrected, because the reference detector detects X-rays from the reference portion, which, due to the equal values of the take-off angles and fan angles of the main beam and reference beam, has the same spectral characteristics as the main portion of the X-rays, which can for example be used to illuminate the object to be imaged (a patient).

The reference detector 108 may comprise energy-resolving photon counters, capable of detecting the spectrum of the instant flux. In photon counting detectors, X-ray photons are counted individually and their energy is measured. To count individual photons, a direct conversion material and a fast-counting ASIC are used, enabling the processing of the charge cloud formed by individual X-ray photons in the direct conversion material. Photon counting is known to allow a lower dose to be used because counting is less susceptible to electronic noise. Of course, other X-ray detection technologies can also be used for the reference detector, such as conventional scintillator-photo detector detection means.

It will be appreciated that in the illustrated embodiment, the reference detector is a two-dimensional pixel matrix. However, in an alternative embodiment, the reference detector could be a pixel line array. A line array would simply measure the X-ray flux across one plane of the reference portion.

According to an exemplary embodiment of the invention, the X-ray tube housing assembly 132 comprises a plurality of reference beams. In this case, each reference beam may have an reference detector 108 which can be electronically selected according to the measurement regime, and/or to optimize a quality parameter of the reference beam.

According to an exemplary embodiment of the invention, the reference detector is of the same type as the detector applied at an imaging side to measure the main portion. If the filters in the reference beam or reference beams are of the same type as the detector applied at an imaging side to measure the main portion, and the detectors on the imaging and reference detector side are also the same, the reference signal received at the reference detector 108 will more accurately characterize the main beam.

According to an exemplary embodiment of the invention, parts of the reference detector or the entire reference detector are placed behind combinations of X-ray filters and attenuators. In an example, a single filter value can be used. However, provision can be made for combinations of filters and attenuators of different values. Such examples will be described subsequently.

Typically, the reference detector is placed between 5 to 10 cm away from the focal spot. This means that X-rays arriving at the reference detector will have considerably more X-ray flux than X-ray flux arriving at an imaging detector placed behind an object to be imaged by the main portion.

Therefore, in an alternative exemplary embodiment of the invention, attenuators may be inserted to take account of this effect. The attenuators allow for a proper selection of those lines of detectors, which are well-illuminated despite varying technique factors, such as voltage.

It will be appreciated that the reference detector 108 can sample the spectral characteristics of the source at a high frequency. Such a frequency is related to the angular rotation speed of the rotating anode. In modern rotating anode tubes, the standard number of revolutions can range from between 3000 revolutions per minute up to 12000 revolutions per minute. Characteristic dwell times of the electron beam on the passing anode material are in the range of tens of microseconds. The sampling of the spectral characteristics of the source should therefore correspond to this frequency in such a way that useful information can be derived from the reference beam.

The variations which will be detectable in the spectrum at such a high frequency may originate from pits and cracks caused in the surface of the rotating anode by the repeated application of an electron beam to the rotating anode at high intensity.

In an alternative embodiment or in addition to the tracking of such defects, the reference detector may also detect thermal effects caused by the heating of the rotating anode. The heating of the rotating anode may be expected to occur over a time frame of several seconds after the application of the electron beam during an exposure. The heating will cause the rotating anode to change geometry.

Therefore, the emitted X-ray flux will move track through the main portion and the reference portion accordingly. This effect may be tracked so that it can be corrected for. Because the reference portion is taken from the same rotating anode as the main portion, and under the assumption that the take-off angle and fan angle of the reference portion are equal to the take-off angle and fan angle of the main portion, the disadvantageous effects caused by the thermal modification of the rotating anode manifested as the movement of the X-ray flux across the reference portion can be compensated for in the main portion, and indeed can be tracked over the duration of an exposure. The compensation can be provided through electron beam deflection means in the X-ray tube, or mathematically during reconstruction (post-processing) of the image from raw projection data, or both.

Of course, the correction of the variation of the focal spot position due to thermal heating of the rotating anode may be performed in real-time, using a control-loop and further beam-positioning electrodes in the X-ray tube, or alternatively the variation of the focal-spot position may be corrected in post-processing of images after an exposure, using a recorded version of the reference signal.

Figure 2:
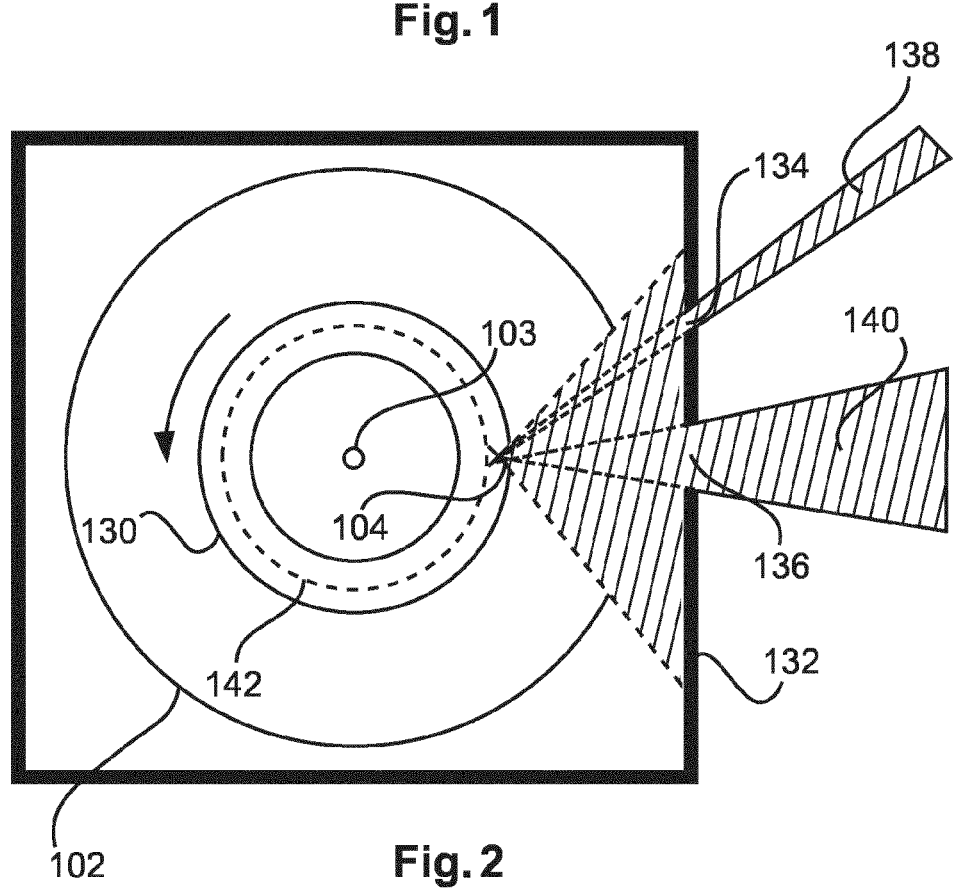
FIG. 2 schematically illustrates a cross-section through an X-ray tube housing assembly according to a further example.

According to a further exemplary embodiment, an X-ray tube housing assembly 132 is provided, comprising an X-ray housing 132 with a reference X-ray window 134 and a main X-ray window 136, so that in operation the reference X-ray window 134 provides a reference beam 138 and the main X-ray window 136 provides a main beam 140. It will be seen that FIG. 2 illustrates a rotating anode 102 viewed from above. The rotating anode is contained inside an X-ray tube 102. The rotating anode 130 may comprise a chamfered edge distinguished by the circular dotted line in FIG. 2. The chamfer is also shown as element 142. The cathode (not shown in this figure) emits a beam of electrons so as to impinge on the chamfered edge of the rotating anode at a focal spot 104, thus causing X-rays to be emitted. It will be appreciated that due to the "heel effect", radiation will be produced over a wide area. A portion of this radiation is illustrated by the grey-shaded area in FIG. 2.

It will be appreciated, as described previously, that the radiation emitted from the focal spot 104 may be considered as being divided into at least a reference portion 112 and main portion 110, and provided the reference detector and a patient detector sample the X-rays using common take-off angles and fan angles, the spectral characteristic at the reference portion and spectral characteristics at the main portion will be the same.

As illustrated in FIG. 2, the X-ray tube 102 is surrounded by an X-ray tube housing 132 which is opaque to X-rays, with the exception of at least a main window (aperture) 136 and a reference window (aperture) 134. The main window 136 and the reference window 134 shape the X-rays of the main portion and the reference portion into a main beam 140 and a reference beam 138, respectively. Therefore, these windows, which are also known in the art as apertures, form well-defined beams for directing X-rays at the reference detector and at the object to be imaged (patient).

The skilled reader will appreciate that it is not essential for the beams to be so defined. Indeed, provided the previously discussed conditions: that the reference portion has a take-off angle which is equal to the main portion and the reference portion has a fan angle which is equal to the main portion, the reference portion may be used to correct information from the main portion.

Figure 3A:
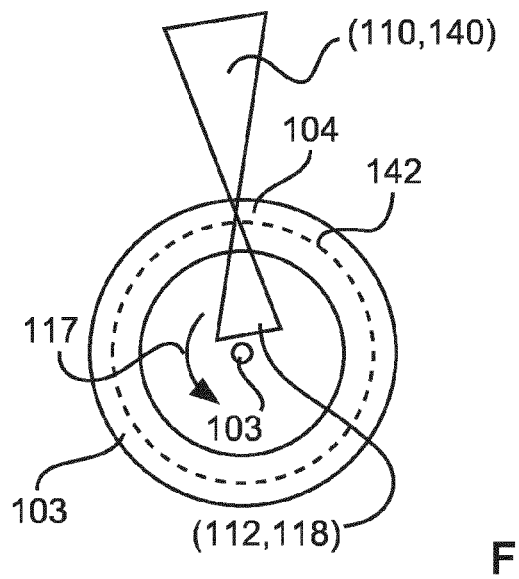
FIG. 3A is an example of a main beam and a reference beam when viewed from above a rotating anode.

FIG. 3A illustrates a rotating anode from above. In this case, a main beam is emitted from the focal spot 104 in a direction outside of the rotating anode, and a reference beam 138 is emitted from the focal spot in an opposite direction to the main beam 110 towards the inside of the X-ray tube. This is intended to show that, in principle, provided the minimum take-off angle of the reference portion 116 of the reference beam equals the minimum take-off angle of the main portion 110 or the main beam 140 and provided that fan angle β of the reference portion 138 and the main portion 140 are equal, the positioning of the reference beam or the reference portion is flexible.

Figure 3B:
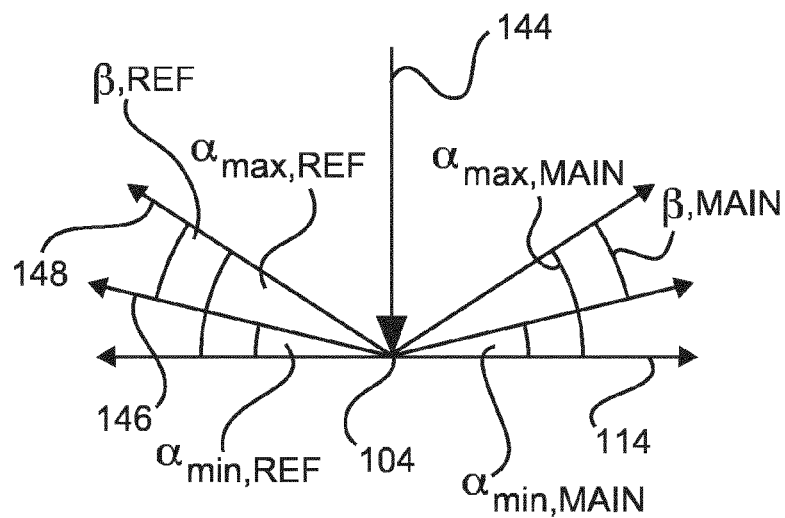
FIG. 3B is an example of geometrical relationships between the relevant angles in a rotating anode X-ray tube according to one example.
Figure 3C:
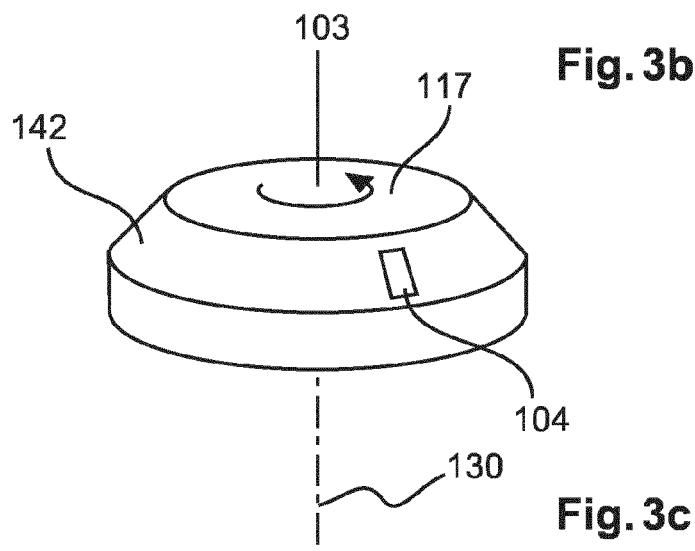
FIG. 3C is a general view of a rotating anode, showing the focal spot.

FIG. 3B further illustrates the geometrical aspects of the invention according to an exemplary embodiment. The base plane 114 is coplanar with the focal spot area, and the azimuth angle defined as the normal to the focal spot area through the center of the focal spot. Orthogonal to the base plane 114 is a line representing the impinging electron beam 144. At 104 is a vertex which represents the location of the focal spot at which the electron beam impinges on the rotating anode. On the left hand of the diagram is a middle line and an outer line 148 defining the extent of the reference portion. Therefore, the angle $\alpha_{min,REF}$ is the minimum take-off angle of the reference beam or the reference portion. The angle $\alpha_{max,REF}$ is the maximum take-off angle of the reference portion. These angles are subtended by the base plane 114. Subtracting $\alpha_{min,REF}$ from $\alpha_{max,REF}$ yields $\beta_{REF}$. A similar definition applies to the angles of the main portion or the main beam, as illustrated in FIG. 3B. A yet further example of the location of the main portion or main beam and the reference portion or reference beam is illustrated in FIG. 4.

Figure 4:
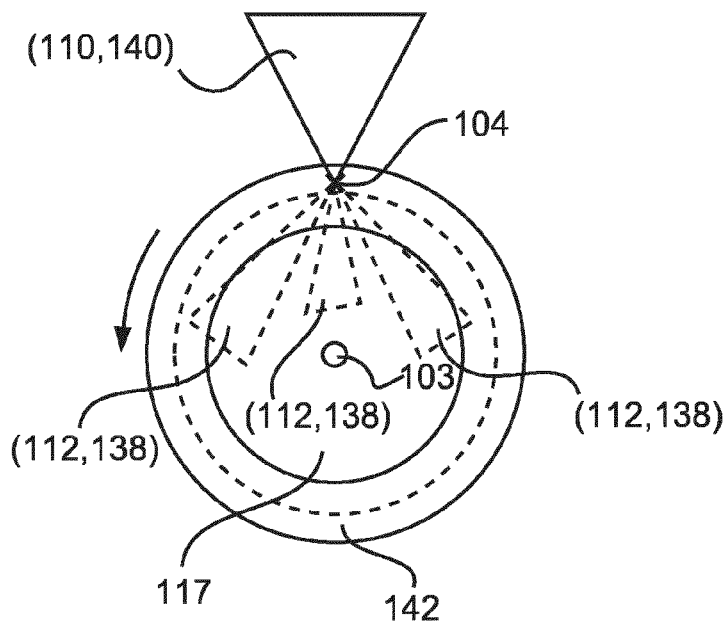
FIG. 4 is a further example of alternative reference portion positions.

FIG. 4 illustrates a top view looking down onto a rotating anode 130, as also discussed in FIG. 3A. In this case, reference beams or reference portions 112 and 138 are shown at optional positions around the focal spot 104. It will be appreciated that these are optional locations for the reference portion or reference beam, and may be used provided the minimum take-off angle of the reference beam or portion is equal to the minimum take-off angle of the main beam or main portion and the fan angle of the reference beam or portion is equal to the fan angle of the main beam or portion.

According to an embodiment, multiple reference beams may be used, if multiple reference detectors 108 are provided.

The precise shape of the reference beam or the reference portion will depend on the location and shape of the reference detector or window 132 of the X-ray housing, respectively.

Figure 5A:
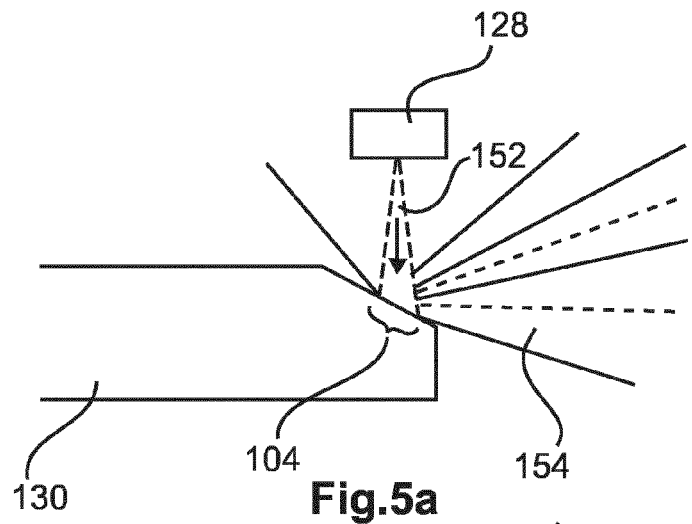
FIG. 5A is a representative view of a rotating anode with a chamfered edge.

In a yet further illustrative example as shown in FIG. 5A, a rotating anode 130 with a chamfered edge is shown in a cut view. A cathode 128 applies a beam of electrons to the chamfered edge. Rapid deceleration of electrons causes X-rays to be emitted in all directions above the anode. Owing to the fact that the X-rays penetrate different distances through the material at the chamfered edge, the emission of the X-rays is random, causing a hemispherical intensity distribution illustrated in FIG. 5B, item 150. This kidney-shaped intensity distribution 150 above the surface of the focal track which is isotropic at larger angles with respect to the focal track surface that declines steeply with small angles at the heel is referred to as the "heel effect".

Figure 5B:
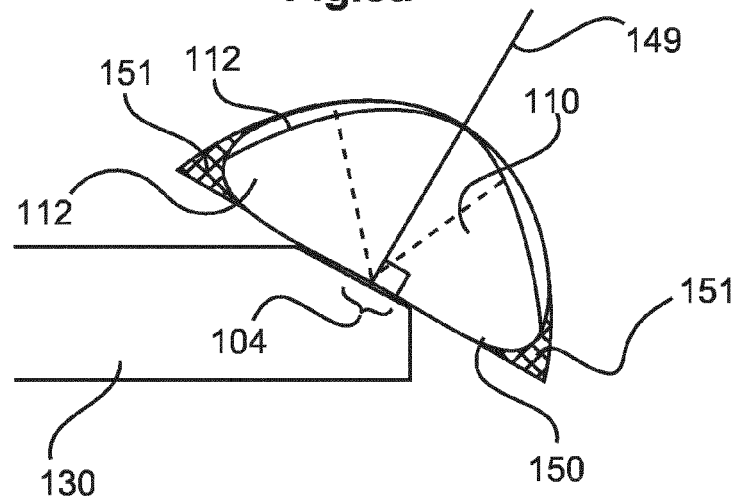
FIG. 5B is a representation of a rotating anode showing an X-ray emission characteristic.

As illustrated in FIG. 5B, the main portion and a reference portion are defined in the kidney-shaped heel characteristics 150 and 151.

In an alternative embodiment, an alternative reference geometry may be considered, but it must be appreciated that this has no bearing on the physical principles involved, and is merely a more convenient way of discussing the geometry when a frusto-conical (chamfered) anode is used. FIG. 6 illustrates a rotating anode 130 with a focal spot located on a chamfered edge. A main portion 110 and a reference portion 112 are emitted from the focal spot 104.

Figure 7:
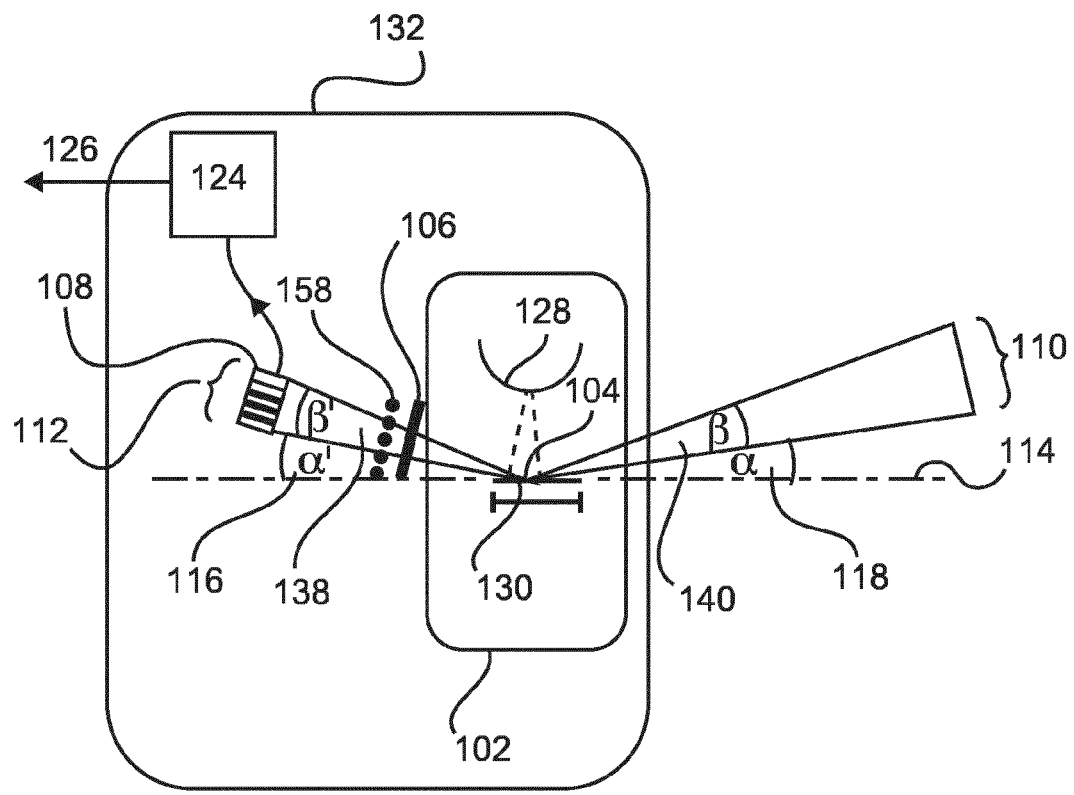
FIG. 7 schematically illustrates a reference detector arrangement.

FIG. 7 illustrates an example of the X-ray tube housing assembly 132 which is the same as that defined in FIG. 1 and described in the associated description with the addition of a attenuator 158 placed in-between the reference filter and the reference detector 108.

The attenuator 158 compensates for the difference in X-ray flux caused by the difference in proximity from the focal spot to the imaged object (and the image-side detector); and from the focal spot to the reference detector 108. The photon flux is reduced by the attenuator, in order to avoid saturating the reference detector 108.

An attenuator is comprised from materials with low atomic numbers, for example, carbon, beryllium, or Teflon®. These materials have a low X-ray filtration effect, but a significant X-ray attenuation effect.

Thus, pile-up and therefore saturation in the pixels of the photon counter or other detector in the reference detector 108 are prevented, thus allowing it to detect X-ray flux, and hence the tube voltage, current, spatial X-ray characteristic, and spectrum accurately.

According to a further exemplary embodiment, the X-ray tube housing assembly 132 may comprise a reference filter 106 which can be substituted between exposures. The substitution may be performed manually by an operator by changing a reference filter slide inside the X-ray tube housing assembly 132.

Additionally, a substitution of the reference filter 106 could be performed automatically by a filter-changing mechanism, such as a filter wheel or a linear filter slide.

Different measurement regimes use different exposure powers, dependent for example on the volume of the object to be imaged. Substitution of the object imaging filter allows an acceptable object image to be recorded, whilst minimizing the patient dose.

As stated previously, it is an aspect of one embodiment of the invention that a filter at the imaging-side matches the reference filter 106, so that the reference beam and the main beam have been exposed to identical conditions, as far as possible. Therefore, in any system where it is envisaged that the imaging filter can be changed in response to the imaged object, there should accordingly be provision to substitute the reference filter 106.

According to an alternative embodiment, the reference filter 106 may be different to a filter used on the imaging side, to compensate for the differences in X-ray flux caused by the different distances between the X-ray tube and the reference detector and the imaging side.

According to an alternative embodiment, multiple sets of reference detectors and filters may be used, in which every reference detector is equipped with a different X-ray filter, which matches with at least one filter used in the main beam.

The attenuator 158 serves to avoid pile-up in the respective pixels of the reference detector 108 behind it. The signals from the reference detector, after an appropriate calculation has been applied, are the reference to correct data from the post-patient detector, which are not subject to over-radiation, because the patient reduces the intensity of the X-ray flux.

Figure 8:
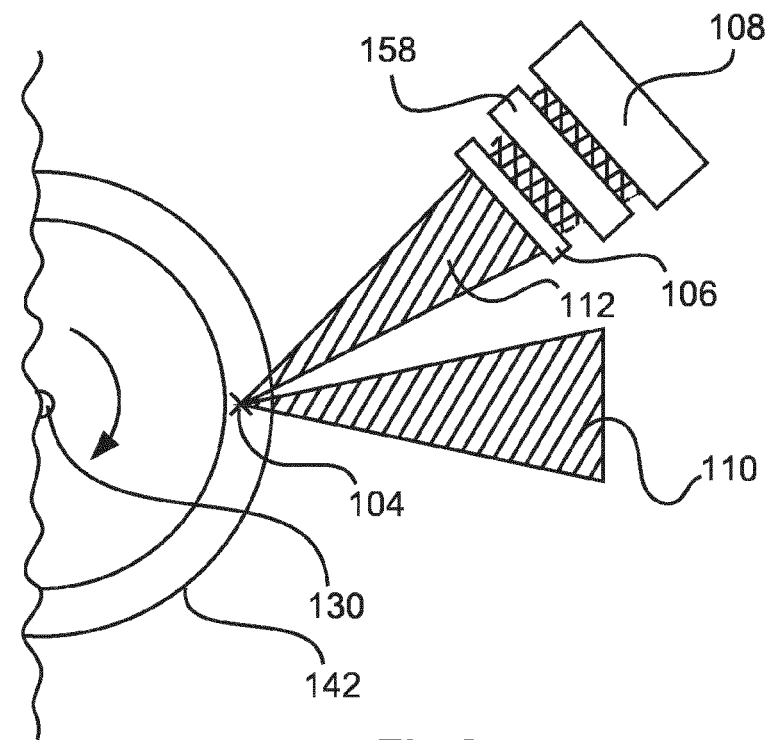
FIG. 8 illustrates further aspects of X-ray detection according to an exemplary embodiment.

FIG. 8 is a further illustrative example of the previously described embodiment, showing a portion of a reference anode 130 from above, additionally comprising a chamfered edge 142. Emitted from the focal spot 104 are a main portion 110 and a reference portion 112 which may also be formed into a main beam and a reference beam by apertures in the housing, which are not shown. In the path of the reference portion are a reference filter 106, an attenuator 158, and finally a reference detector 108.

Figure 9:
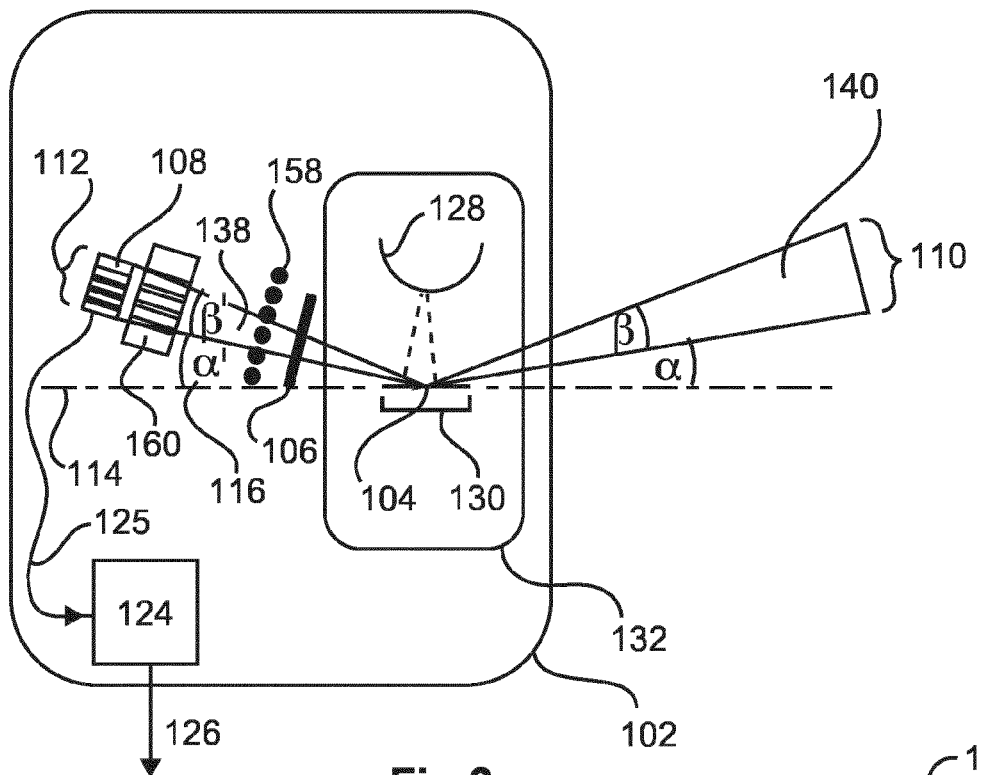
FIG. 9 is a schematic representation of an exemplary embodiment of a reference detector arrangement.

FIG. 9 illustrates a further exemplary embodiment showing an example of the X-ray tube housing assembly 132 comprising an anti-scatter grid 160 located in-between the reference detector 108 and the attenuator 158, and further focused onto the focal spot. The anti-scatter grid 160 can be made from leaves or sheets of metal. The function of the anti-scatter grids is to focus the reference beam after it leaves the attenuator. The anti-scatter grid only allows beams directly emitted from the focal spot to be incident on the reference detector.

Figure 10:
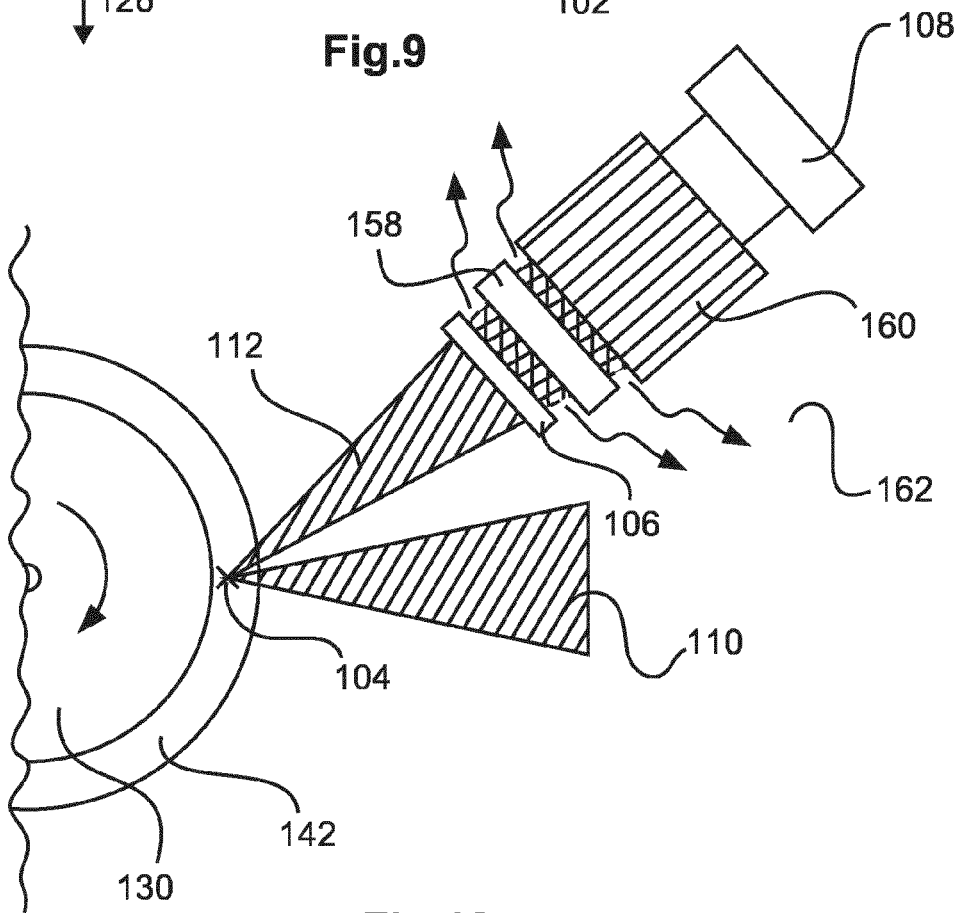
FIG. 10 illustrates further aspects of X-ray detection with a reference detector according to an example.

FIG. 10 further illustrates the anti-scatter grid 160 in operation. FIG. 10 shows a downward view onto a portion of a rotating anode 130 with a chamfer 142 and a focal spot 104, from which a main portion 110 and a reference portion 112 are emitted. The reference portion 112 then passes through the reference filter 106 and the attenuator 158. The scattering effect of the reference filter and the attenuator causes the X-rays of the reference beam to be scattered, as shown by the lines 162 between 156 and 160. If the scattered X-rays were admitted into the reference detector, undesirable artefacts not directly caused by imperfections of the rotating anode could remain in the reference signal and therefore harm the quality of any image which was corrected using the signal calculated from the reference signal.

Therefore, the anti-scatter grid provided in-between the attenuator 158 and the reference detector 108 prevents scattered radiation from reaching the reference detector 108.

Figures 11A, 11B:
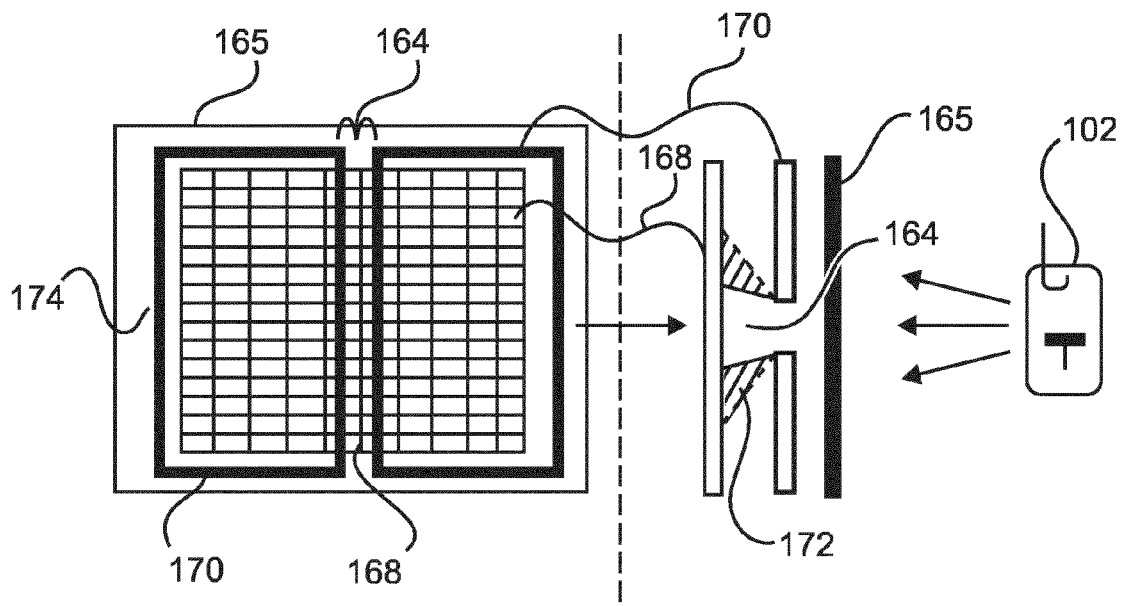
FIG. 11A is a schematic representation of a one-dimensional focal spot slit camera according to an example.
FIG. 11B illustrates further aspects of the one-dimensional focal spot slit camera of FIG. 11B shown from the side.

According to an exemplary embodiment of the invention, FIG. 11A shows a one-dimensional focal spot slit camera for use in an X-ray tube housing assembly 132.

The one-dimensional focal spot slit camera further comprises an X-ray blocker 170, wherein the X-ray blocker 170 comprises a spatial resolving slit 164, and is thus configured together with the reference detector 108 to form a one-dimensional focal spot slit camera 174 to detect the position of the focal spot 104 from an edge of an intensity distribution of the reference beam.

The X-ray blocker 170 is typically implemented using a sheet of metal with a slit in it, although it will be appreciated that any material opaque to X-rays may form the X-ray blocker.

According to a further embodiment, the X-ray blocker may additionally or alternatively comprise an opaque wire or wires.

According to a further embodiment, the X-ray blocker may additionally or alternatively comprise a combination of spatial resolving slits and wires.

According to a further embodiment, the one-dimensional focal spot slit camera may comprise an extra X-ray filter, to generate a desired spectrum on the reference detector.

A two-dimensional pixel array 168 is positioned behind the X-ray blocker 170. As shown in FIG. 11B, the area of the two-dimensional pixel array 168 underneath the gap in the attenuator 164 has a direct line of sight to the focal spot of the X-ray tube housing assembly 132. Therefore, the one-dimensional focal spot slit camera can measure the relative displacement position of the focal spot in one direction.

Furthermore, the one-dimensional focal spot slit camera may comprise a filter attenuator 165. The filter attenuator 165 is a sheet of material with a low atomic number such as carbon, beryllium, or Teflon®. These materials have a low X-ray filtration effect, but a significant attenuation effect. The filter attenuator is required, as in previous embodiments, to reduce the excessive photon flux from the X-ray source. In addition, the spectral characteristic across the fan-angle direction of the reference beam can still be measured with a one-dimensional slit. The focal spot position information can be derived from pixels in the slit area. Beam spectral information, or photon flux, can still be derived from pixels not underneath the slit area.

Even though the centre pixels under the slit 164 may be subject to over-radiation at high total photon fluxes, the focal spot is wider than the slit, and there will be pixels with sufficiently readable signals which allow detection of the position of the focal spot in one dimension from the edge of the intensity distribution.

It will be appreciated that the position of the focal spot need not only be derived from the edge of the intensity distribution.

According to an alternative embodiment, an analysis of a pattern of the intensity distribution of the reference beam detected by the reference detector 108 may be performed by the controller. Using this analysis, the location of the focal spot may be tracked. Any suitable analysis method capable of resolving areas of differing intensity into a focal spot position may be used. Alternatively, the controller may output the pattern so that the analysis may be performed in post processing.

According to a further exemplary embodiment of the invention, a pattern of an intensity distribution may be defined as the edge of the intensity distribution.

According to an exemplary embodiment, the pixel array 168 is replaced with a one-dimensional pixel strip, and could be used in a more basic detector to detect the deviation of the position of the focal spot in one dimension only, and not to derive spectral information from other areas of the beam.

According to an embodiment of the invention, an X ray tube assembly is provided with opaque wires placed in front of the reference detector to form a spatial resolving stripe, which is thus configured, together with the reference detector, to detect a position of the focal spot from a pattern of an intensity distribution.

According to a further embodiment of the invention, an example of the X-ray tube housing assembly 132 may be provided with two spatial resolving slits 176, 178 in the X-ray blocker 170, which are positioned orthogonally to form a two-dimensional focal spot slit camera 180, which is configured to detect, in operation, the position of the focal spot from of the pattern of the measured reference beam.

Figure 12A:
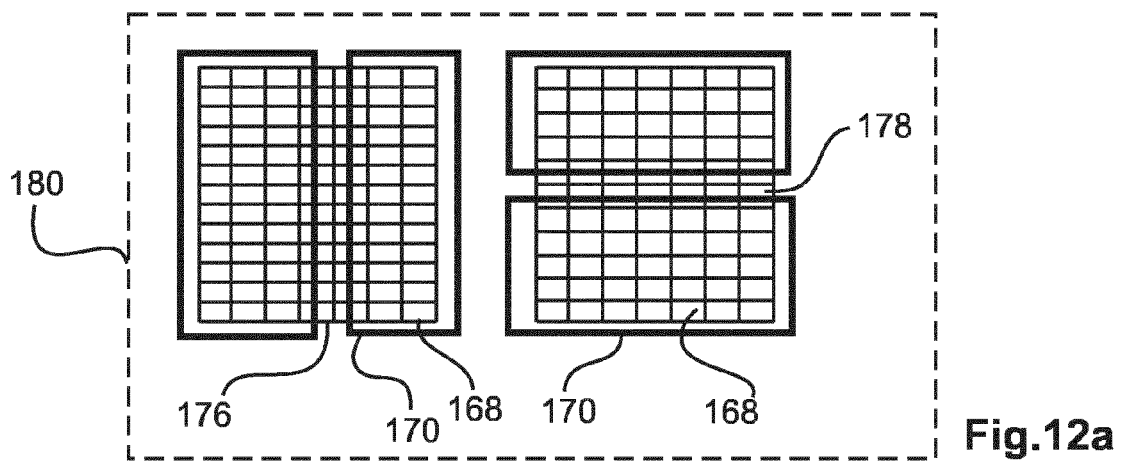
FIG. 12A illustrates a first alternative embodiment of a two-dimensional focal spot slit camera.

A first alternative of this embodiment is illustrated in FIG. 12A. A one-dimensional focal spot slit camera, as disclosed in FIG. 11A and described previously is positioned next to a further one-dimensional focal spot slit camera. These cameras are the same in construction to the focal spot slit camera as described in FIG. 11A. Each one-dimensional focal spot slit camera comprises an X-ray blocker 170 positioned in front of the pixel array 168. Each X-ray blocker has a central slit 164.

According to a first alternative of the two-dimensional focal spot slit camera two, one-dimensional focal spot slit cameras may be placed side by side with the slit 176 of the first camera, being perpendicular to the slit 178 of the second one-dimensional focal spot slit camera. It will be appreciated by the person skilled in the art that the arrangement shown in FIG. 12A is only an example and the second one-dimensional focal spot slit camera may be positioned on any of the other three sides of the first one-dimensional focal spot slit camera, provided the slits 176 and 178 are orthogonal to each other.

In the embodiment as illustrated in FIG. 12A, the variation of the focal spot in the radial and axial directions along the edge of the rotating anode can be detected. In addition, the spectral information across the entire beam can be detected. Such an arrangement can detect the position and size of the focal spot. In other words, the presence of two orthogonal slit cameras positioned across the fan beam allows the focal spot drift along the azimuth and above and below the azimuth to be detected, so that the position of the focal spot can be identified in two dimensions.

Figure 12B:
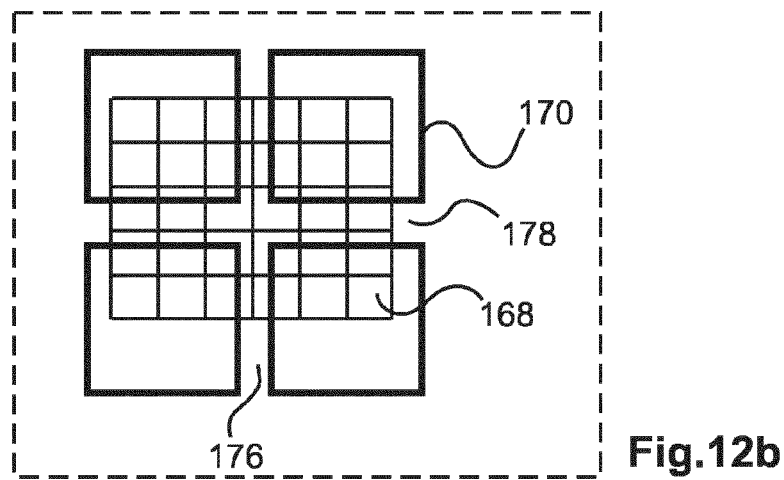
FIG. 12B illustrates a second alternative embodiment of a two-dimensional focal spot slit camera.

An alternative embodiment is shown in FIG. 12B. In this case, a focal spot slit camera is provided using just one of the two-dimensional pixel arrays 168. The two orthogonal slits are, in this case, provided over the single pixel array 168, by taking an X-ray blocker 170 as previously described, and adding an extra slit perpendicular to the first slit. It will be appreciated that with the correct positioning such a single, two-dimensional focal spot slit camera may detect the radial and axial position of the focal spot, without needing to use two detectors, as in the embodiment disclosed in FIG. 12A. In this way, the detection of the position of the focal spot can be performed more efficiently. There is not a requirement to provide two, two-dimensional pixel arrays 168.

Figure 13A:
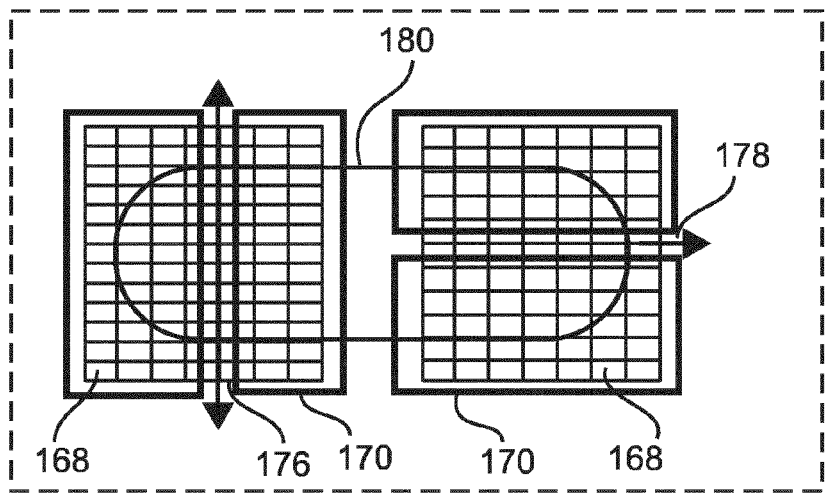
FIG. 13A illustrates the two-dimensional focal spot slit camera of FIG. 12A in use.

FIG. 13A illustrates the first alternative of the two-dimensional focal spot slit camera in operation. The line 180 represents an energy contour of an X-ray beam pattern incident on the two-dimensional focal spot slit camera. The shape of this contour is dependent on the focal spot shape and position.

A purely radial deviation of the focal spot on the rotating anode will cause a commensurate change in the angle of elevation of the main beam and the reference beam. This will be projected onto the two-dimensional focal spot slit camera. The left portion of the two-dimensional focal spot slit camera in FIG. 13A detects such a radial deviation as a vertical movement of a contour of the X-ray beam up and down the detector.

Likewise, a purely axial deviation of the focal spot on the rotating anode in an axial direction will result in a sideways deviation of the contour which can be detected by the camera on the right hand side of FIG. 13A.

By careful positioning of the two-dimensional focal spot slit camera, any deviations in the location of the focal spot can be detected.

Figure 13B:
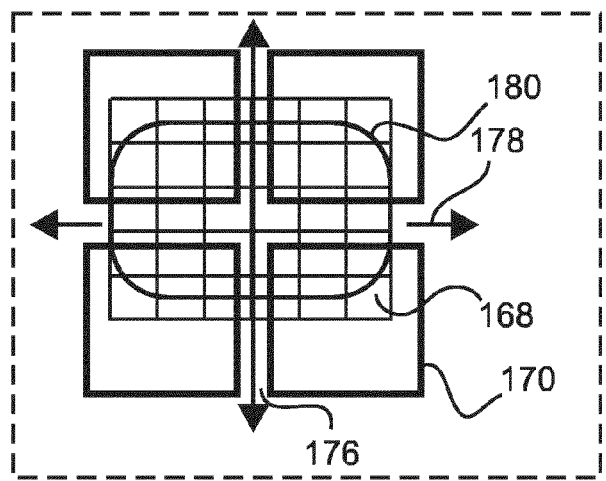
FIG. 13B illustrates the two-dimensional focal spot slit camera of an alternative embodiment of FIG. 12B in use.

FIG. 13B shows the second alternative of the two-dimensional focal spot slit camera design in operation. A beam contour 180 is again shown superimposed on the second alternative of the two-dimensional focal spot slit camera. The same processes as previously described give rise to similar deviations of the contour on the surface of the two-dimensional focal spot slit camera, and these can again be detected by the pixel array 168.

According to a further embodiment, the reference filter of the X-ray tube housing assembly 132 has a reference filter 106 with a plurality of filters 185 with different filter values (185; A, B, C) and the one- or two-dimensional focal spot slit cameras comprise a further plurality of attenuators 184 (X and Y) which are each provided with a range of different attenuator values, so that the reference detector of the slit camera detects the reference beam behind a plurality of combinations of attenuator and filter values.

Figure 14:
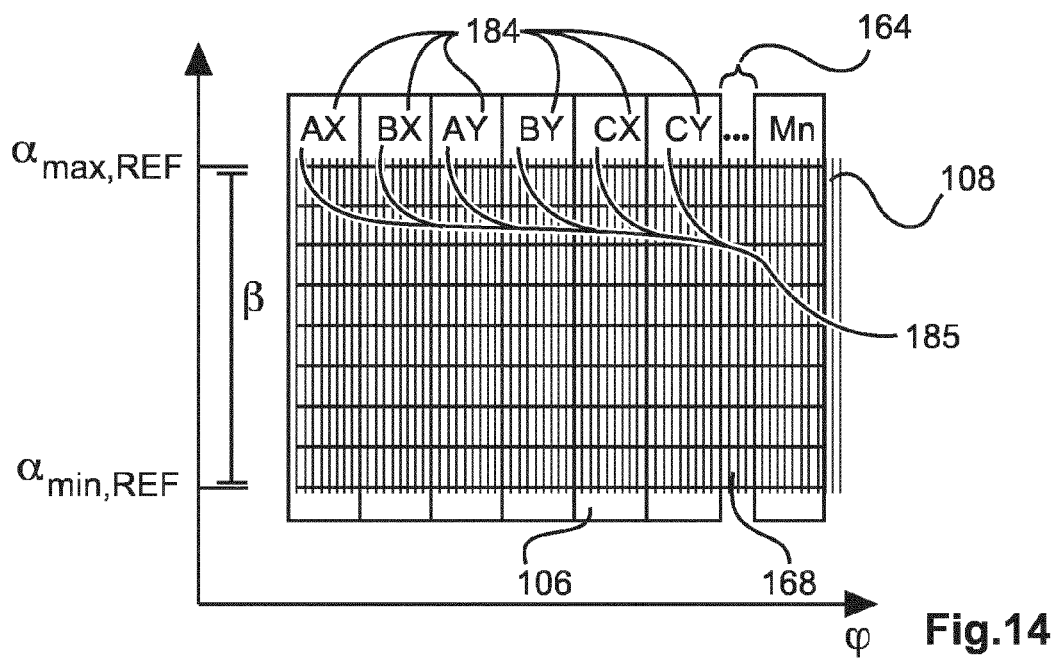
FIG. 14 illustrates a reference filter according to an example, comprising a plurality of filters with different filter values and different attenuators, wherein the filter and attenuator combinations cover the entire fan beam.

In FIG. 14, the orientation of the focal spot slit camera with a plurality of filters and attenuators is shown with respect to axes which demonstrate the orientation of the camera. It will be seen that the arrangement of the attenuators and filters covers the entire reference beam in the angle of elevation direction; that is to say, that the detector is so positioned that the pixel array intersects the angle of elevation $\alpha_{min,REF}$ and $\alpha_{max,REF}$, and the pixel array is illuminated over the entire fan angle $\beta$.

In the azimuth direction $\phi$ (in the base plane), the range of combinations of filter and attenuator values is illuminated by the X-ray reference beam. In the azimuth direction, there is a slit 164 present, as in the focal spot slit cameras previously described. Therefore, filter and attenuator combinations are provided which cover the entire fan beam $\beta$. There may be M multiplied by N combinations of M different filters 185 and N different attenuators 184. As previously stated, filters in the main beam, used for imaging, are changeable. According to this embodiment, for each possible filter used in the main beam, there will be a corresponding reference filter illuminated by the reference beam. In FIG. 14, the character A, B, or C represents a filter value, and the character X or Y represents a attenuator value.

The additional attenuator values are proposed because the photon flux from the X-ray source may vary according to the application protocol of the X-ray system This solution also ensures that there is always a well-illuminated line array of reference detectors positioned along the reference fan beam $\beta'$, which are neither over- nor under-radiated. A well-illuminated detector line can then be selected by a controller.

Therefore, the additional attenuators allow for a proper selection of those lines of detectors that are well-illuminated, despite widely varying technique factors.

According to an embodiment, spectral information may still be derivable from pixels covered by filter values not related to a present measurement technique factor, although an allowance will need by the controller for the combinations of different filter and attenuator values in this case.

According to a further embodiment of the invention, an X-ray tube housing assembly 132 is provided, wherein the filter (A, B, C) and the attenuator combinations (X,Y) cover the entire reference fan beam $\beta'$. Therefore, for each possible filter in the used beam, there will be a corresponding filter in the reference beam. The spectrum can be measured across the width of the beam.

According to a further exemplary embodiment, an X-ray tube housing assembly is provided comprising a plurality of one-dimensional or two-dimensional focal spot slit cameras, together forming a multi-slit focal spot camera, wherein a first and a second slit of the slits of the plurality of one- or two-dimensional focal-spot slit cameras are offset relative to a pixel boundary of the reference detector 108.

This embodiment takes into account the fact that the pixels of the reference detector 108 may have a comparatively wide pitch, when the much smaller distance between the reference detector and the focal spot is taken into account (compared with the greater distance between the object to be imaged and the focal spot).

This embodiment may be applied either to the one dimensional, or two dimensional slit camera embodiment. The key idea is that at least one slit is offset relative to a pixel boundary of the detector 108.

To use pixels with a wide pixel width close to the source, the slits of the focal spot camera should be positioned near to the borders of the detector pixels.

In this way, motion of the focal spot can be detected as changes of the signal ratio between both pixels. If a plurality of one- or two-dimensional focal spot slit cameras are provided, each slit having a different relative position of the slits with respect to the position of the detector pixels behind, it is easier to measure the focal spot position in various practical positions. The "sub-camera" with the highest sensitivity to motion of the focal spot would be selected. The sub-camera outputs would differ by the ratio of signals between adjacent detector pixels.

Figure 15:
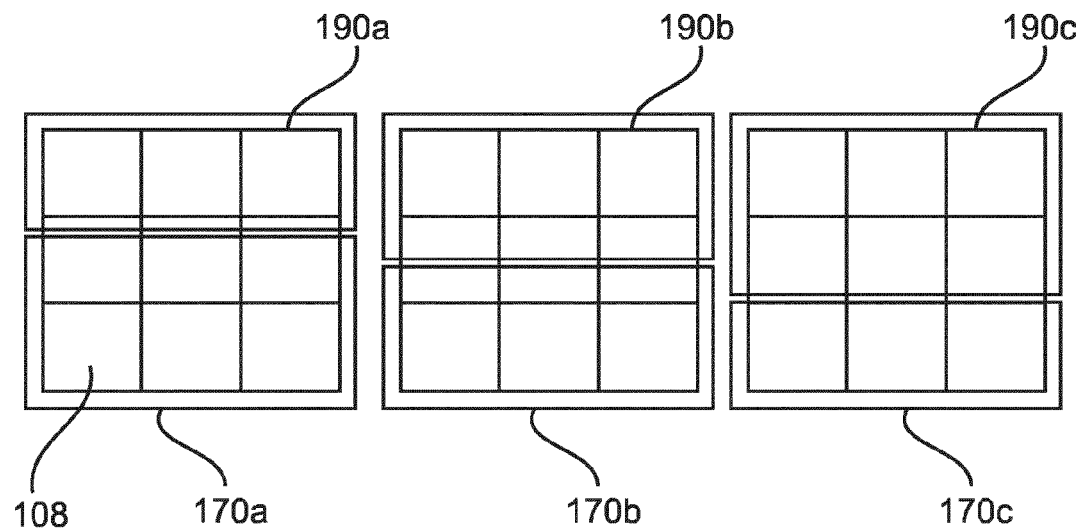
FIG. 15 shows an example of a one-dimensional multi-slit focal spot camera with offset slits.
Figure 16:
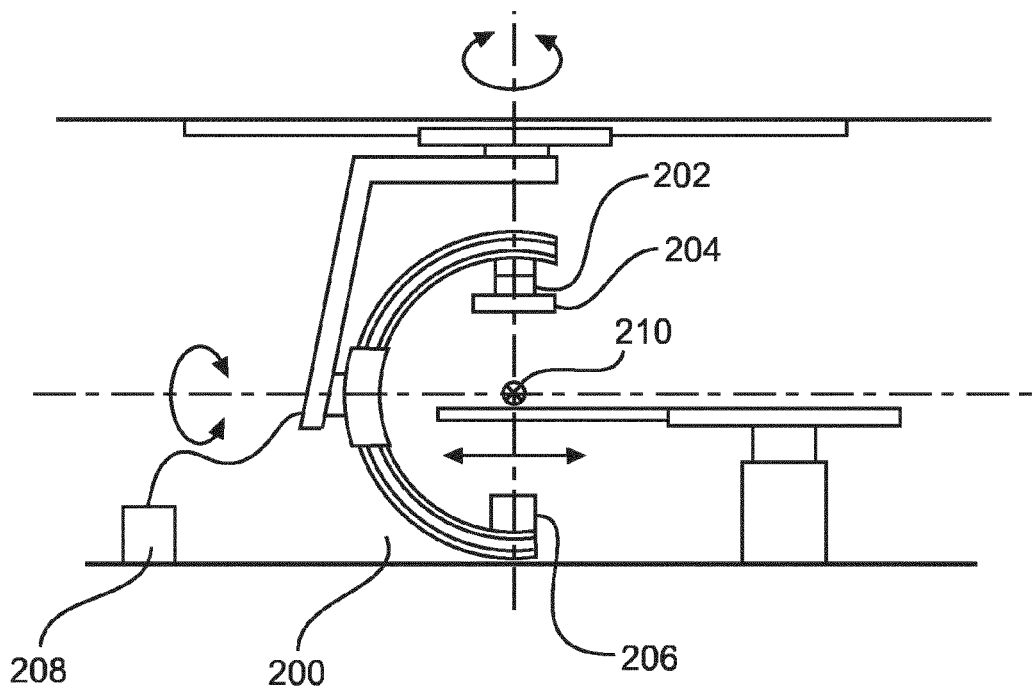
FIG. 16 illustrates an example of a C-arm X-ray imaging system.
Figure 17:
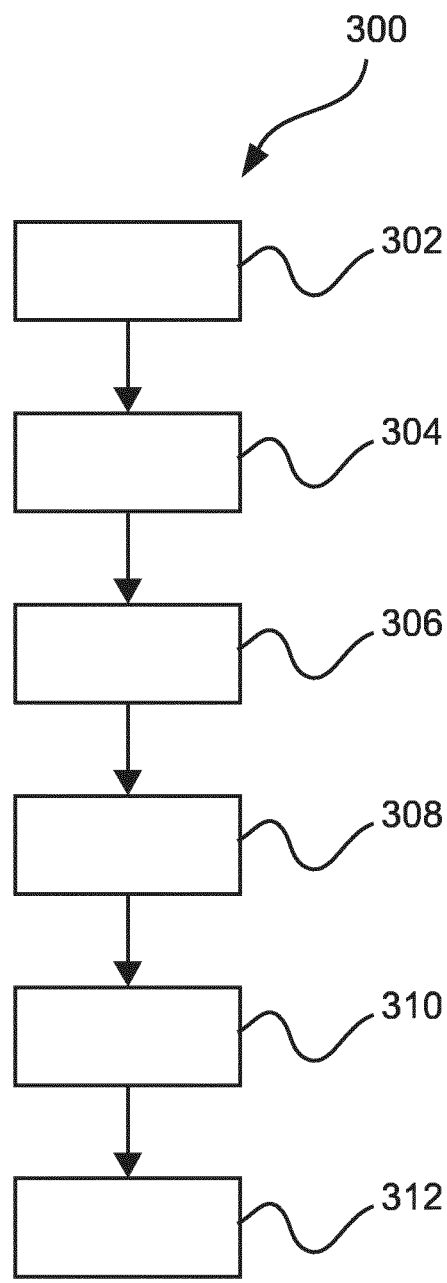
FIG. 17 illustrates an X-ray imaging method according to an example.

FIG. 15 illustrates three one-dimensional focal spot slit cameras according to this embodiment. The reference detectors 108 of this embodiment have a comparatively large pixel pitch. The X-ray blocker 190a has a slit close to the top boundary of the middle pixel row. The X-ray blocker 190b has a slit close to the middle of the middle pixel row of the reference detector. The X-ray blocker 190c has a slit close to the bottom boundary of the middle pixel row of the reference detector.

According to a further exemplary embodiment of the invention, multiple slits can be placed in front of the reference detector, which have different spatial position relative to the pixel borders behind, thus forming a "multi-slit focal spot camera". The projection of each slit, as taken from the centre of the focal spot at rest, would be located in a different position relative to an underlying border line between detector pixels. In other words, the detector pixel pitch may differ from the slit pitch, as projected from the focal spot onto the detector.

Upon movement or changing shape of the focal spot, these multiple of slit cameras would generate different signal ratios, which would be outputted. An optimal signal ratio may be used for detection of the distortion.

According to a further exemplary embodiment, the controller 124 of the X-ray tube housing assembly 132 is configured to calculate from at least one output 125 of at least one reference detector 108 at least one parameter from the group consisting of: spectral variability, tube voltage, the position of the focal spot, the size of the focal spot, the intensity of the focal spot, the tube current, the tube ageing, the dynamic anode rotational instability, the periodic anode rotational instability, magnetic distortions of the position or shape of the focal spot, and gravitational distortions of the shape or position of the focal spot.

According to this embodiment, calibration signals for spectral detection can be calculated which can take into account imperfections of the rotating anode occurring at a high frequency, caused usually by rotating anode damage. The spectral detection across the entire reference beam can be used to correct the image derived from a main beam taken from the same source.

In addition, changes occurring at a slower rate due mainly to the heating at the rotating anode may be tracked. The drift of the focal spot may thus be compensated for in the image detected from the main beam and reconstructed. In addition, the signals defining the motion of the focal spot due to anode heating may also be fed back to a closed loop control system which may correct the direction of the electron beam using additional positioning means like electrodes or magnetic dipoles inside the X-ray tube to correct focal spot drift.

According to an embodiment of the invention, the correction of excess flux or pile-up, may be performed by selecting a reference detector pixels for correction of the projection data which, due to the attenuator, experiences a similar flux rate to post main beam pixel, for which the data have to be corrected. In addition, the correction can take into account the take-off angle.

In this case, a reference detector pixel, or group of pixels, is selected for correction of the data from the main beam. This pixel, or group of pixels, should be positioned at the same take-off angle as the pixel for which the data have to be corrected.

The benefits of this approach are that compact high frequency calibration signals for spectral detection, detection of tube ageing caused by track erosion and arcing, and focal spot characteristics can be detected. Small tube currents, which may be at or below 1 mA, can be measured at the X-ray tube housing assembly 132. Currents which do not contribute to the X-ray generation are excluded. Furthermore, a bulky, resistive voltage divider is not needed, as is required in the state of the art.

Another advantage of this measurement system is that parasitic degrading effects can be quantified, such as off-focal field emission, polarization and conduction of cable insulation, and micro-discharges in the X-ray tube.

Furthermore, because the detection unit is mounted at the source, there is abundant X-ray flux for signal transmission. Therefore, the reference beam may have a significantly better signal to noise ratio (SNR) than the main beam.

If combined with a spatial resolving array detector, as previously discussed, the unit can also measure focal spot size and intensity distribution in parallel, and allow for stabilization of the key parameters, focal spot size, and tube current.

The X-ray tube housing assembly 132 according to the previously described embodiment can calibrate the projected data in the main beam recorded behind a target object.

According to a further exemplary embodiment of the invention, the X-ray tube housing assembly 132 may contain the reference filter 106 and reference detector 108 within the vacuum tube of the X-ray tube housing assembly 132.

By placing the reference detector and reference filter inside the vacuum tube, the reference beam arrangement can be made more compact.

According to an exemplary embodiment of the invention, there is provided an X-ray tube housing assembly according to any preceding claim, wherein a plurality of reference beams is provided, wherein each of the plurality of reference beams is associated with a reference detector, and wherein the tube housing assembly is configured, in operation, to select or to combine signals from the plurality of reference beams.

According to a further exemplary embodiment of the invention, there is provided an X-ray imaging system 200, with: an X-ray tube housing assembly 202, a changeable pre-object X-ray filter 204, a post-object detector 206; and a processing unit 208. The X-ray tube housing assembly 202 is an X-ray tube housing assembly according to one of the previously described embodiments. The pre-object X-ray filter 204 matches at least one reference filter value in the X-ray tube housing assembly 202. The post-object detector 206 is the same type as the reference detector 108 in the X-ray tube housing assembly 202, and the processing unit 124, 208 receives the correction signals from the X-ray tube housing assembly 202, 100 and uses them to correct data from the post-object detector 206.

In this embodiment, the reference beam is exposed to the same elements as the main beam used for imaging. In other words, the reference filter of the X-ray tube housing assembly 202 matches the pre-object X-ray filter 204. In addition, the detector type of the reference detector 108 in the X-ray source 100 is of the same design as the post-object detector 206. The processing unit 208 calibrates the data received from the main beam behind the imaged object 210. The correction takes into account excess flux rate (pile-up correction) in which a reference detector pixel is selected for correction of projected data which behinds its attenuator experiences a similar flux rate as the post-patient pixel for which data have to be corrected. Alternatively, the reference detector pixel is selected for correction of projection data of which is pixel is positioned at the same take-off angle as the pixel of which the data have to be corrected.

It will be appreciated that the technique described previously which can be summarized as taking a reference beam which is not affected by the object to be imaged, and deriving from the reference beam signals to be used for correction of signals received from behind the objects 210 to be imaged by the post-object detector need not only be applied to a C-arm imaging system. Indeed, in principle, this technique is also applicable to any system using X-rays. For example, mammography X-ray, a CT scanner, and a fluoroscopy system, could all benefit from the use of this technique.

According to an alternative embodiment of an X-ray imaging system 200, the reference filter of the X-ray tube housing assembly 202 does not match the pre-object X-ray filter 204.

In this case, differences of beam flux (caused by the proximity of the reference detector to the X-ray tube), and the object for imaging can be compensated for.

According to another exemplary embodiment of the invention, a method 300 is provided for determining changes in the X-ray emission characteristic of an X-ray tube. The method comprises the steps of:

Generating 302 X-radiation by emitting electrons from a cathode, so that they impinge at a focal spot on a rotating anode, wherein the X-radiation comprises a main portion, and a reference portion, wherein the main portion is distinct from the reference portion; wherein the main portion and the reference portion are between a minimum ($\alpha_{min,MAIN}$, $\alpha_{min,REF}$) and a maximum ($\alpha_{max,MAIN}$, $\alpha_{max,REF}$) reference take-off angle, being angles of elevation from a vertex at the focal spot, subtended by a base plane. The minimum and maximum take-off angles of the reference portion and the main portion are equal.

The method then comprises a step of filtering 304 the reference portion using a reference filter.

Then, there is a step of detecting 306 the reference portion.

The method then comprises a step of outputting 308 a reference signal representing a characteristic of the reference portion.

Then, the method comprises a step of calculating 310 a signal from the reference signal.

Finally, the method comprises the step of outputting 312 the signal.

The generating step 302 is also referred to as step a), the filtering step 304 is also referred to as step b), the detecting step 306 is also referred to as step c), the step of outputting the reference signal 308 is also referred to as step d), the calculating step 310 is also referred to as step e), and the step of outputting the correction signal 312 is referred to as step f).

It will be appreciated that variations in the X-rays caused by the X-ray tube housing assembly can be measured and corrected, because of the step 306 of detecting the reference portion of the X-rays, which has the same spectral characteristics as the main portion of the X-rays, which can, for example, be used to illuminate a patient. This is because the main portion and the reference portion are taken from the same source, and the angles of elevation from the base plane of the source anode, and the fan angles, are the same.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray tube housing assembly operable to provide a signal, the X-ray tube housing assembly comprising:
an X-ray tube generating X-radiation from a focal spot;
a reference filter; and
a reference detector; and
a controller;
wherein the X-radiation comprises a main portion, and a reference portion, wherein the main portion is distinct from the reference portion;
wherein the main portion and the reference portion are between a minimum ($\alpha_{min,MAIN}$, ($\alpha_{min,REF}$) and a maximum ($\alpha_{max,MAIN}$, $\alpha_{max,REF}$) take-off angle, being angles of elevation from a vertex at the focal spot (104), subtended by a base plane;
wherein the minimum take-off angles of the reference portion and the main portion ($\alpha_{min,REF}$, $\alpha_{min,MAIN}$) are equal to each other, and the maximum take-off angles of the reference portion and the main portion are equal to each other ($\alpha_{max,REF}$, $\alpha_{max,MAIN}$);
wherein the reference filter is configured to filter the reference portion before detection of the reference portion by the reference detector;
wherein the reference detector is configured to detect the reference portion to provide a reference signal; and
wherein the controller is configured to calculate a signal, based on the reference signal.

2. X-ray tube housing assembly according to claim 1, wherein the X-ray tube housing assembly comprises an X-ray housing with a reference X-ray window and a main X-ray window, so that, in operation, the reference X-ray window provides a reference beam, and the main X-ray window provides a main beam.

3. X-ray tube housing assembly according to claim 1, wherein the X-ray tube housing assembly comprises an object opaque to X-rays placed inside a rotating anode X-ray tube, so as to separate the X-radiation into the reference beam and the main beam.

4. X-ray tube housing assembly according to claim 1, wherein the X-ray tube housing assembly further comprises an attenuator placed in-between the reference detector (108) and the reference filter.

5. X-ray tube housing assembly according to claim 4, wherein the reference filter can be substituted between exposures.

6. X-ray tube housing assembly according to claim 4, comprising an an anti-scatter grid focused onto the focal spot and located in-between the reference detector and the attenuator.

7. X-ray tube housing assembly according to claim 1, further comprising an X-ray blocker with a spatial resolving slit, which is thus configured, together with the reference detector, to form a one-dimensional focal spot slit camera to detect a position of the focal spot from an edge of an intensity distribution.

8. X-ray tube housing assembly according to claim 1, further comprising opaque wires placed in front of the reference detector to form a spatial resolving stripe, which is thus configured, together with the reference detector, to detect a position of the focal spot from a pattern of an intensity distribution.

9. X-ray tube housing assembly according to claim 7, wherein two spatial resolving slits are positioned orthogonally to form a two-dimensional focal spot slit camera, which is configured to detect, in operation, the position of the focal spot from of a pattern of the measured reference beam.

10. X-ray tube housing assembly of claim 7, wherein the reference filter comprises a plurality of filters with different filter values, and the one- or two-dimensional focal spot slit cameras comprise a further plurality of attenuators with different attenuator values, so that the reference detector of the slit camera detects the reference beam behind a plurality of combinations of attenuators and filters.

11. X-ray tube housing assembly of claim 10, wherein the filter and the further attenuator combinations cover the entire reference beam.

12. X-ray tube housing assembly according to claim 7, wherein a plurality of one-dimensional or two-dimensional focal spot slit cameras is provided, together forming a multi-slit focal spot camera, wherein at least a first and a second slit of the slits of the plurality of one- or two-dimensional focal-spot slit cameras are offset relative to a pixel boundary of the reference detector.

13. X-ray tube housing assembly according to claim 1, wherein the controller is configured to calculate from at least one output of at least one reference detector, at least one parameter from the group consisting of: spectral variability, tube voltage, the position of the focal spot, the size of the focal spot, the intensity of the focal spot, the tube current, the tube ageing, the dynamic anode rotational instability, the periodic anode rotational instability, magnetic distortions of the position or shape of the focal spot, and gravitational distortions of the shape or position of the focal spot.

14. X-ray tube housing assembly according to claim 1, wherein the reference filter and the reference detector are arranged within the envelope of the rotating anode X-ray tube.

15. X-ray tube housing assembly according to claim 14, wherein a plurality of reference beams is provided, wherein each of the plurality of reference beams is associated with a reference detector, and wherein the tube housing assembly is configured, in operation, to select or to combine signals from the plurality of reference beams.

16. An X-ray imaging system, with:
an X-ray tube housing assembly;
a changeable pre-object X-ray filter;
a post-object detector;
a processing unit;
wherein the X-ray tube housing assembly is an X-ray tube housing assembly according to claim 1;
wherein the pre-object X-ray filter matches at least one reference filter in the X-ray tube housing assembly;
wherein the post-object detector is the same type as the reference detector in the X-ray tube housing assembly, and
wherein the processing unit receives the correction signals from the X-ray tube housing assembly and uses them to correct data from the post-object detector.

17. X-ray imaging system of claim 15, wherein the pre-object X-ray filter is different from the at least one reference filter in the X-ray tube housing assembly.

18. A method for determining a signal representing changes in the X-ray emission characteristic of an X-ray tube housing assembly, comprising the steps of:
a) generating X-radiation from the focal spot of an X-ray tube,
wherein the X-radiation comprises a main portion, and a reference portion, wherein the main portion is distinct from the reference portion; wherein the main portion and the reference portion are between a minimum ($\alpha_{min,MAIN}$, $\alpha_{min,REF}$) and a maximum ($\alpha_{max,MAIN}$, $\alpha_{max,REF}$) take-off angle, being angles of elevation from a vertex at the focal spot, subtended by a base plane; wherein the X-radiation comprises a main portion, and a reference portion, wherein the minimum take-off angles of the reference portion and main portion ($\alpha_{min,REF}$, $\alpha_{min,MAIN}$) are equal to each other, and the maximum take-off angles of the reference portion and main portion are equal to each other ($\alpha_{max,REF}$, $\alpha_{max,MAIN}$);
b) filtering the reference portion using a reference filter;
c) detecting the reference portion;
d) outputting a reference signal representing a characteristic of the reference portion;
e) calculating a signal; and
f) outputting the signal.

* * * * *